US009040286B2

(12) United States Patent
Zon et al.

(10) Patent No.: US 9,040,286 B2
(45) Date of Patent: May 26, 2015

(54) DIAGNOSIS AND TREATMENT OF CANCER

(75) Inventors: Leonard I. Zon, Wellesley, MA (US); Craig Ceol, Sherborn, MA (US); Yariv J. Houvras, New York, NY (US)

(73) Assignee: CHILDREN'S MEDICAL CENTER CORPORATION, Boston, MA (US)

( * ) Notice: Subject to any disclaimer, the term of this patent is extended or adjusted under 35 U.S.C. 154(b) by 216 days.

(21) Appl. No.: 13/147,713

(22) PCT Filed: Feb. 3, 2010

(86) PCT No.: PCT/US2010/022994
§ 371 (c)(1),
(2), (4) Date: Oct. 11, 2011

(87) PCT Pub. No.: WO2010/091049
PCT Pub. Date: Aug. 12, 2010

(65) Prior Publication Data
US 2012/0020953 A1    Jan. 26, 2012

Related U.S. Application Data

(60) Provisional application No. 61/149,498, filed on Feb. 3, 2009, provisional application No. 61/260,476, filed on Nov. 12, 2009.

(51) Int. Cl.
*C12M 3/00* (2006.01)
*C12N 9/10* (2006.01)
*G01N 33/53* (2006.01)
*C07K 16/40* (2006.01)
*C12N 15/113* (2010.01)
*G01N 33/574* (2006.01)

(52) U.S. Cl.
CPC ............ *C07K 16/40* (2013.01); *C12N 15/1137* (2013.01); *C12N 2310/14* (2013.01); *C12Y 201/01043* (2013.01); *G01N 33/574* (2013.01); *G01N 2333/91011* (2013.01)

(58) Field of Classification Search
CPC .. C12Q 1/6886; C12Q 1/6809; C12Q 1/6816; C12Q 1/485; C12Q 1/68; C12Q 1/708; C12Q 1/682; C12Q 1/6851; C12Q 1/6813; C12Q 1/6874; C12Q 1/6876; C12Q 1/37; C12Q 1/42; C12Q 1/48; A61K 38/00; A61K 39/00; A61K 39/0011; A61K 39/395; A61K 51/1027
See application file for complete search history.

(56) References Cited

FOREIGN PATENT DOCUMENTS

WO    2009/147445    12/2009

OTHER PUBLICATIONS

Sun et al., Oncoproteomics of hepatocellular carcinoma: from cancer markers' discovery to functional pathways. Liver Internatl., p. 1021-1038, 2007.*
Li et al., J Biol Chem, 281(28):19489-19500 (2006). "The histone methyltransferase SETDB1 and the DNA methyltransferase DNMT3A interact directly and localize to promoters silenced in cancer cell."
Spannhoff, The International Journal of Biochemistry & Cell Biology, 41(Issue 1):4-11 (2009). "Cancer treatment of the future: inhibitors of histone methyltransferases."
Wang et al., Molecular Cell, 12:475-487 (2003). "mAM facilitates conversion by ESET of dimethyl to trimethyl lysine 9 of histone H3 to cause transcriptional repression."
Watanabe et al., Cancer Cell International, 8(15):1-12 (2008). "Deregulation of histone lysine methyltransferases contributes to oncogenic transformation of human bronchoepithelial cells."

* cited by examiner

*Primary Examiner* — Elly-Gerald Stoica
(74) *Attorney, Agent, or Firm* — David S. Resnick; Nixon Peabody LLP

(57) ABSTRACT

Provided herein are methods for diagnosing cancer by determining the level of expression of SETDB1 in a biological sample. Also provided herein are methods for treating cancer by administering an inhibitor of SETDB1 to a subject in need thereof.

13 Claims, 14 Drawing Sheets

A.

B.

C.

2A.

2B.

2C.

2D.

4A.

4B.

| Candidate oncogene | Median tumor onset (wks) | No. animals | p value |
|---|---|---|---|
| SETDB1 trial 1 | 13 | 34 | $1.7 \times 10^{-4}$ |
| SETDB1 trial 2 | 12 | 36 | $1.4 \times 10^{-5}$ |
| SETDB1 average | 12 | 70 | $9.4 \times 10^{-7}$ |
| EGFP trial 1 | 19 | 61 | n/a |
| EGFP trial 2 | 19 | 31 | n/a |
| EGFP trial 3 | 18 | 33 | n/a |
| EGFP average | 19 | 125 | n/a |
| ARNT | 18 | 70 | 0.09 |
| CDC42SE1 | 22 | 64 | 0.04 |
| ECM1 | 21 | 40 | 0.86 |
| ENSA | 23 | 61 | 0.05 |
| FAM63A | 20 | 66 | 0.65 |
| LASS2 | 24 | 43 | 0.03 |
| MLLT11 | 23 | 63 | 0.07 |
| MRPL9 | 22 | 64 | 0.49 |
| PIK4CB | 22 | 74 | 0.74 |
| PIP5K1A | 21 | 53 | 0.31 |
| POGZ | 17 | 53 | 0.12 |
| PRUNE | 22 | 63 | 0.17 |
| PSMB1 | >25 | 63 | $2.9 \times 10^{-4}$ |
| PSMD4 | 23 | 47 | 0.30 |
| RFX5 | 20 | 35 | 0.40 |
| TARSL1 | 17 | 62 | 0.25 |

7A.

WM1968 BRAF wild-type

```
          600
5' GCT ACA GTG AAA TCT 3'
   CGA TGT CAC TTT AGA
    A   T   V   K   S
```

7B.

WM262 BRAF V600E mutant

```
          600
5' GCT ACA GAA AAA TCT 3'
   CGA TGT CTT TTT AGA
    A   T   E   K   S
```

7C.

A375 BRAF V600E mutant

```
          600
5' GCT ACA GAG AAA TCT 3'
   CGA TGT CTC TTT AGA
    A   T   E   K   S
```

8A.

8B.

DIAGNOSIS AND TREATMENT OF CANCER

CROSS REFERENCE TO RELATED APPLICATIONS

The present application is a 35 U.S.C. §371 National Phase Entry Application of International Application No. PCT/US2010/022994 filed Feb. 3, 2010, which designates the U.S., and which claims the benefit under 35 U.S.C. §119(e) of U.S. Provisional Application No. 61/260,476, filed Nov. 12, 2009, the contents of which are incorporated herein by reference in their entireties.

FIELD OF THE INVENTION

The field of the invention relates to the diagnosis and/or treatment of cancer.

BACKGROUND

Melanoma is a malignant tumor of melanocytes. Primarily it is a skin tumor, but it is also seen, though less frequently, in the melanocytes of the eye (uveal melanoma). Even though it represents one of the rarer forms of skin cancer, melanoma underlies the majority of skin cancer-related deaths. Despite many years of intensive laboratory and clinical research, the sole current effective cure is surgical resection of the primary tumor before it achieves a thickness of greater than 1 mm. If the tumor is more invasive, surgery can be combined with radiation and/or chemotherapy. Since these conventional modalities cannot cure patients of lethal metastasized tumors, efficacy of alternative treatments such as immunotherapy are being investigated in clinical trials. However, currently there is essentially still no cure for advanced stage disease despite decades of research.

SUMMARY OF THE INVENTION

The present invention is based, in part, on the discovery that expression of the histone methyltransferase SETDB1 is increased in melanoma cells. Thus, provided herein are methods for diagnosing cancer (e.g., melanoma) by determining the level of expression of SETDB1. Also provided herein are methods for treating cancer by administering an inhibitor of SETDB1 to a subject in need thereof.

In one aspect, provided herein are methods for facilitating the diagnosis of cancer in a subject, the method comprising: measuring the level of SETDB1 in a biological sample obtained from a subject, wherein an increase in the SETDB1 level in the sample compared to a reference is indicative of cancer in the subject.

In one embodiment of this aspect, the cancer is selected from the group consisting of: melanoma, thyroid, pancreas and lung cancer.

In another embodiment of this aspect, the subject is human.

In another embodiment of this aspect, the level of SETDB1 is detected using an antibody-based binding agent which specifically binds to SETDB1 protein.

In another embodiment of this aspect, the method further comprises administering to the subject at least one anti-cancer agent.

Another aspect described herein relates to methods for treating cancer comprising administering to a subject an inhibitor of SETDB1.

In one embodiment of this aspect, the subject is human.

In another embodiment of this aspect, the method further comprises a step of selecting a subject having cancer.

In another embodiment of this aspect, the selecting step comprises comparing the level of SETDB1 in a sample obtained from a subject to a reference, wherein an increase in SETDB1 level in the sample compared to the reference is indicative of cancer in the subject.

In another embodiment of this aspect, the level of SETDB1 is detected using an antibody-based binding agent which specifically binds to the SETDB1 protein.

In another embodiment of this aspect, the cancer is selected from the group consisting of: melanoma, thyroid, pancreas and lung cancer.

Also described herein are computer readable storage media having computer readable instructions recorded thereon to define software modules including a determination system and a comparison module for implementing a method on a computer for diagnosing a subject with cancer, the method comprising: (a) storing data derived from a biological sample obtained from a subject and which represents expression data for SETDB1 from a biological sample, (b) comparing with the comparison module the data stored on the storage device with reference and/or control data, and to provide a retrieved content, and (c) displaying the retrieved content for the user, wherein the retrieved content is indicative that the subject has cancer if the level of SETDB1 in the biological sample is higher than the reference data, and wherein the retrieved content is indicative that the subject is free from cancer if the level of SETDB1 in the biological sample is lower than the reference data.

Also provided herein are computer systems for obtaining expression data for SETDB1 in a biological specimen comprising: (a) a determination system configured to receive expression information for SETDB1 from a biological sample obtained from a subject; (b) a storage device configured to store data output from the determination system; (c) a comparison module adapted to compare the data stored on the storage device with reference and/or control data, and to provide a retrieved content, and (d) a display module for displaying the retrieved content for the user, wherein the retrieved content is indicative that the subject has cancer if the level of SETDB1 in the biological sample is higher than the reference data, and wherein the retrieved content is indicative that the subject is free from cancer if the level of SETDB1 in the biological sample is lower than the reference data.

Another aspect described herein relates to a kit for measuring SETDB1 expression in a biological sample, the kit comprising: (a) an agent that selectively binds SETDB1, (b) packaging materials and instructions for measuring SETDB1 expression in a sample.

In one embodiment of this aspect, the agent comprises a detectable moiety.

In another embodiment of this aspect, the kit further comprises an SETDB1 positive control.

In another embodiment of this aspect, the kit is an ELISA kit or comprises primers for RT-PCR.

In another embodiment of this aspect, the agent comprises an antibody or a nucleic acid probe.

Also described herein is a method for delaying onset of melanoma in a subject, the method comprising: administering an inhibitor of SETDB1 to a subject suspected of having or diagnosed as having melanoma.

DEFINITIONS

A "subject" in the context of the present invention is preferably a mammal. The mammal can be a human, non-human primate, mouse, rat, dog, cat, horse, or cow, but is not limited to these examples.

As used herein, the terms "sample" and "biological sample" are used interchangeably and refer to a sample of biological tissue, cells, or fluid that, in a healthy and/or pathological state, contains cells. In one embodiment, the biological sample is a biopsy sample from a site of suspected tumor growth (e.g., skin biopsy for melanoma diagnosis). A biopsy sample can include e.g., tissue biopsy, fine needle aspiration, core needle biopsy, vacuum assisted biopsy, open surgical biopsy, among others. In some embodiments a biological sample is taken from a human subject, and in alternative embodiments the biological sample is taken from any mammal, such as rodents, animal models of diseases, commercial animals, companion animals, dogs, cats, sheep, cattle, and pigs, etc.

As used herein, the term "reference" refers to a reference value, or range of values, obtained for SETDB1 from e.g., at least one subject determined to lack detectable cancer. The reference value or range of values can be obtained from a plurality of subjects in a population substantially free of cancer (i.e., cancer is not detectable by typical clinical means). The reference sample can be stored as a value(s) on a computer or PDA device to permit comparison with a value obtained from a subject using the methods described herein. The reference sample can also be obtained from the same subject e.g., at an earlier time point prior to onset of detectable cancer using clinical tests known to those of skill in the art. One of skill in the art can determine an appropriate reference sample for use with the methods described herein. In one embodiment, the reference is obtained from a subject or plurality of subjects having, or diagnosed with having, cancer, such as melanoma.

As used herein, the term "SETDB1" refers to a mRNA or protein product of the SETDB1 gene found on chromosome 1, locus 1q21 (Gene ID: 9869 (human), NCBI database available on the world wide web at ncbi.nlm.nih.gov/sites/gene). The SETDB1 protein comprises histone methyltransferase activity and is also referred to in the literature as ESET; KG1T; KMT1E; KIAA0067; H3-K9-HMTase4; and SETDB1 SET.

As used herein, the term "increase in SETDB1 level" refers to an increase in the expression of SETDB1 of at least 10% in a sample from a subject having cancer compared to a reference, as that term is used herein. In other embodiments, the increase in expression of SETDB1 is at least 20%, at least 30%, at least 40%, at least 50%, at least 60%, at least 70%, at least 80%, at least 90%, at least 95%, at least 1-fold, at least 2-fold, at least 5-fold, at least 10-fold, at least 20-fold, at least 50-fold, at least 100-fold or higher in a biological sample from a subject having cancer than a reference (e.g., a sample from a subject substantially free of cancer).

As used herein, the term "plurality of subjects" refers to at least two subjects (e.g., 2, 3, 4, 5, 6, 7, 8, 9, 10, 20, 30, 40, 50, 60, 70, 80, 90, 100, 500, 1000, 10000 or more subjects).

As used herein, the terms "free from detectable cancer" and "substantially free of cancer" are used interchangeably and refer to subjects that do not exhibit any clinically detectable signs of cancer using routine clinical methods known to those skilled in the art (e.g., routine visual inspection by a health care professional; imaging such as ultrasound, CAT scan, endoscopy, CT scan, MRI; palpation; mammogram; routine biopsy, etc).

As used herein the term "anti-cancer agent" refers to any organic or inorganic molecule, including modified and unmodified nucleic acids such as antisense nucleic acids, RNA interference agents such as siRNA, shRNA, or miRNA; peptides, peptidomimetics, receptors, ligands, and antibodies that is useful in treating cancer.

As used herein, the term "inhibitor of SETDB1" refers to an agent that inhibits the histone methyltransferase activity of SETDB1 by at least 10% in a subject compared to the SETDB1 activity prior to, or in the absence of, administration of the agent. The agent can be any organic or inorganic molecule, including modified and unmodified nucleic acids such as antisense nucleic acids, RNA interference agents such as siRNA, shRNA, or miRNA; peptides, peptidomimetics, receptors, ligands, and antibodies. In some embodiments, a SETDB1 inhibitor reduces the activity of SETDB1 by at least 20%, at least 30%, at least 40%, at least 50%, at least 60%, at least 70%, at least 80%, at least 90%, at least 95%, at least 99%, or even 100% (i.e., no detectable activity of SETDB1) in the presence of the inhibitor compared to the activity of SETDB1 in the absence of the inhibitor. In one embodiment, the inhibitor of SETDB1 is mithramycin (also referred to as plicamycin, MIT) or a derivative thereof.

As used herein, the term "detectable moiety" refers to a molecule, or moiety of a molecule, capable of producing a detectable signal such as e.g., fluorescence, chemiluminescence, a colorimetric signal etc.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth.

Western blot of protein lysates from miniCoopR-EGFP (left) and miniCoopR-SETDB1 (right) melanomas demonstrate minimal differences in the level of BRAFV600E protein levels.

Figure 6:
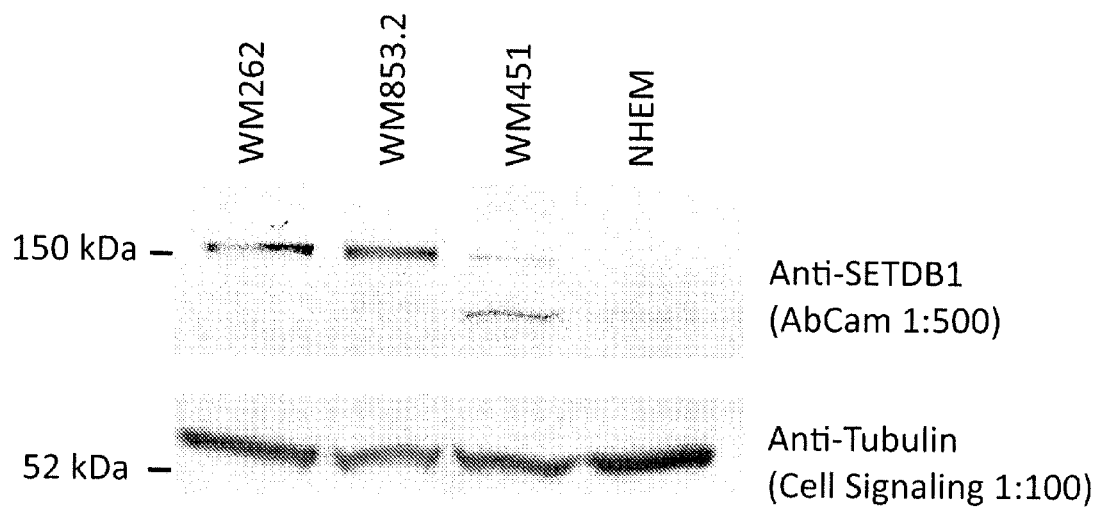

FIG. 6 SETDB1 expression levels in melanoma short-term cultures used in this study Western blot of protein lysates from WM262 (high), WM853.2 (high), and WM451Lu (Low) in comparison with normal human embryonic melanocytes (NHEM), reveal significant differences in SETDB1 protein levels.

Figure 7:
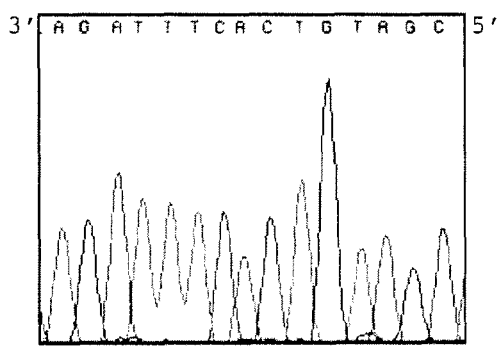
Figure 7:
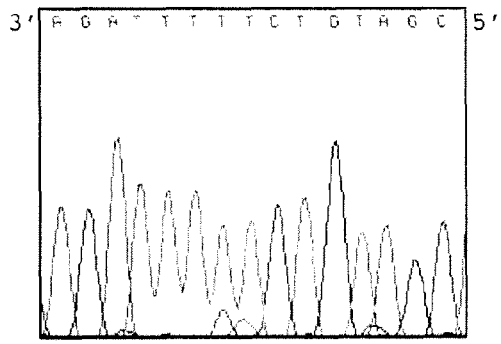
Figure 7:
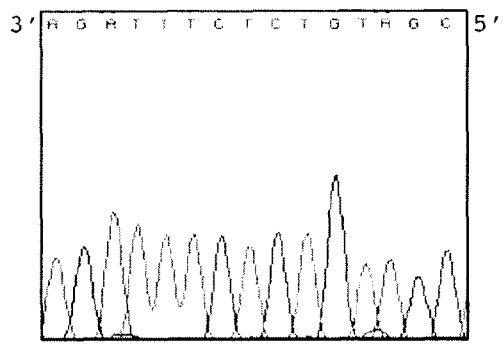

FIGS. 7A-7C The WM262 SETDB1 high short-term culture is BRAFV600E mutant

The SETDB1 high line used for ChIP-Seq, WM262, is BRAFV600E mutant (7B). Control BRAF wild-type (7A) and BRAFV600E mutant (7C) cells are shown. WM451Lu has been previously identified to be BRAFV600E mutant7.

FIGS. 8A and 8B shRNA mediated knockdown of SETDB1 is associated with reduced proliferation. WM262 and WM451Lu were infected with lentiviral vectors encoding SETDB1 or GFP (Control) shRNAs. Melanoma cultures infected with SETDB1 shRNAs showed reduced proliferation as compared with cultures infected with GFP shRNAs.

Figure 9:
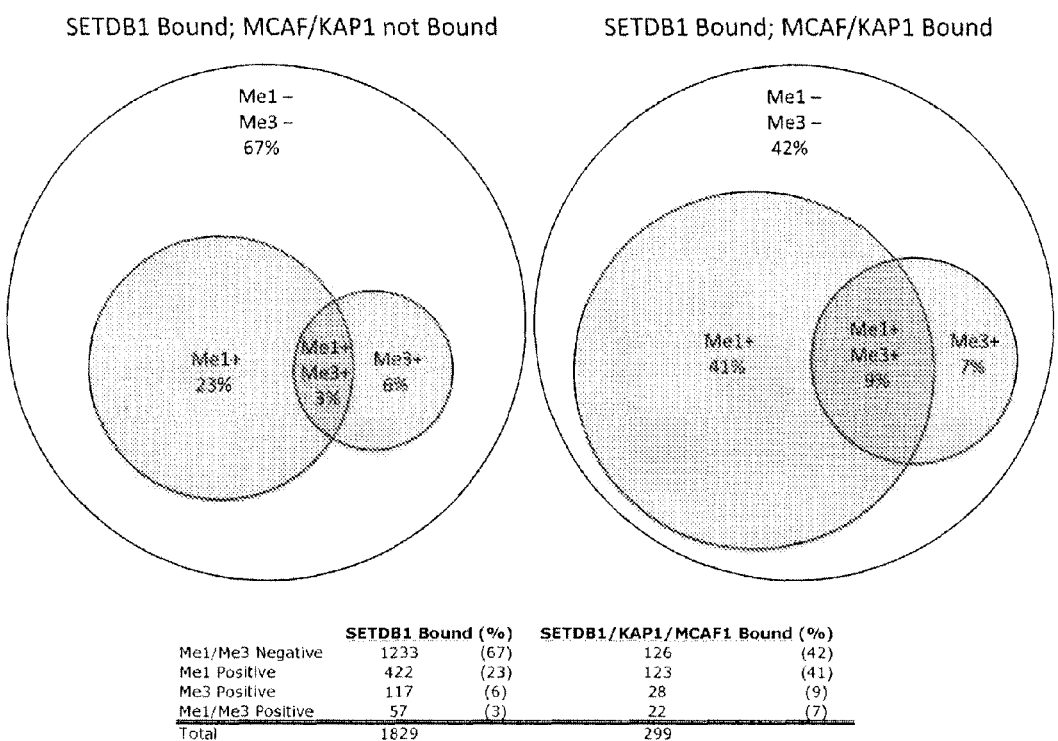

FIG. 9 Binding of SETDB1, MCAF1 and KAP1 is associated with increased H3K9 methylation of promoters. As compared to gene promoters that are bound only by SETDB1, promoters that are bound by SETDB1, MCAF1 and KAP1 are enriched for both H3K9 mono- and trimethylation.

Figure 10:
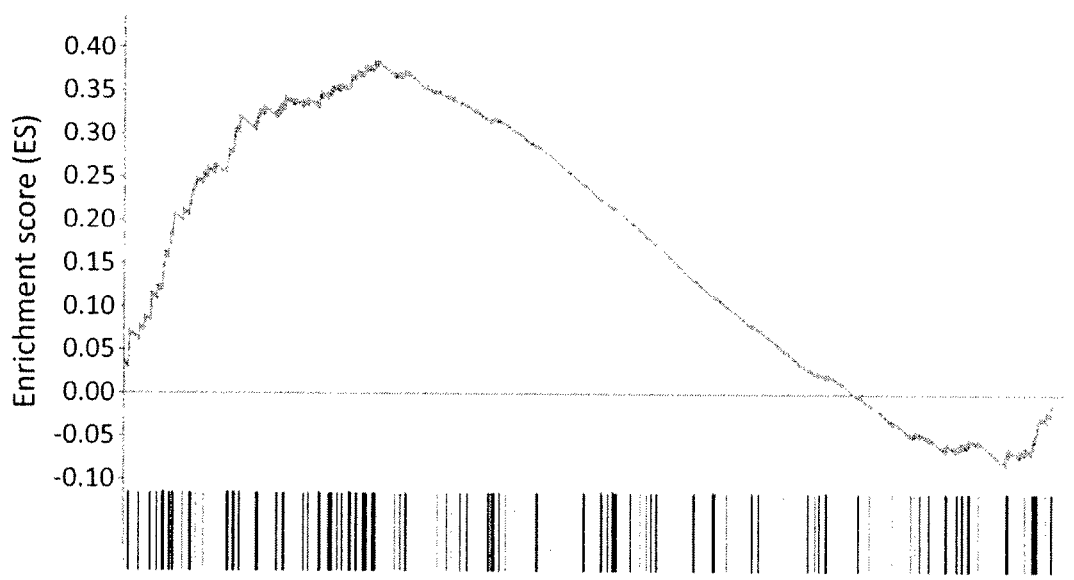

FIG. 10. Gene Set Enrichment Analysis reveals a positive correlation between SETDB1 bound genes in WM262 and SETDB1 Expression levels. All SETDB1 bound genes with peak height greater than 20 which were also not bound by either MCAF1 or KAP1 were selected. The resulting 258 genes show a positive enrichment by GSEA across 93 melanoma short term cultures with SETDB1 expression levels.

Figure 11:
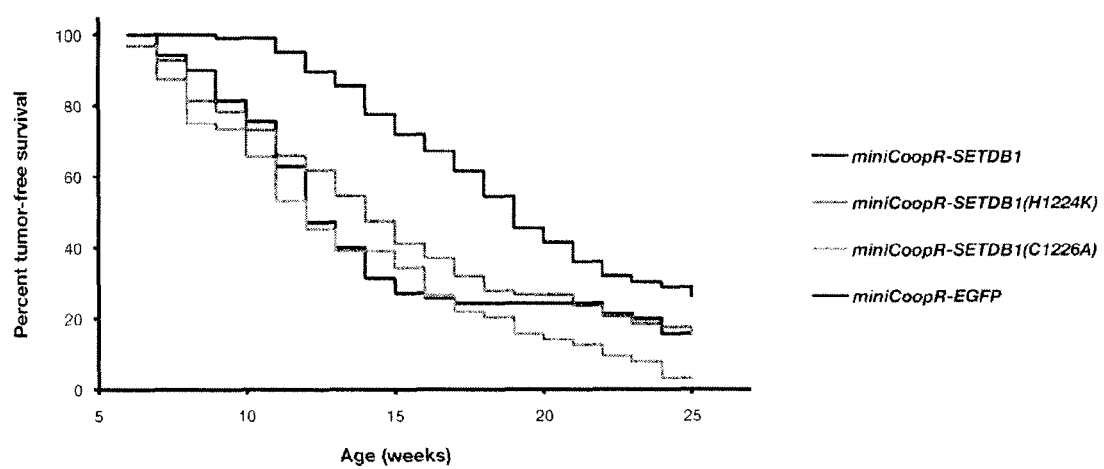

FIG. 11 Overexpression of methyltransferase-deficient SETDB1 variants accelerates melanoma onset Melanoma free survival curves in zebrafish expressing SETDB1(H1224K) and SETDB1(C1226A) methyltransferase-deficient variants as compared to wild-type SETDB1 and the reference miniCoopR-EGFP curve.

Figure 12:

FIG. 12 shows an effect of SETDB1 on histone methylation in a zebrafish model.

Figure 13:
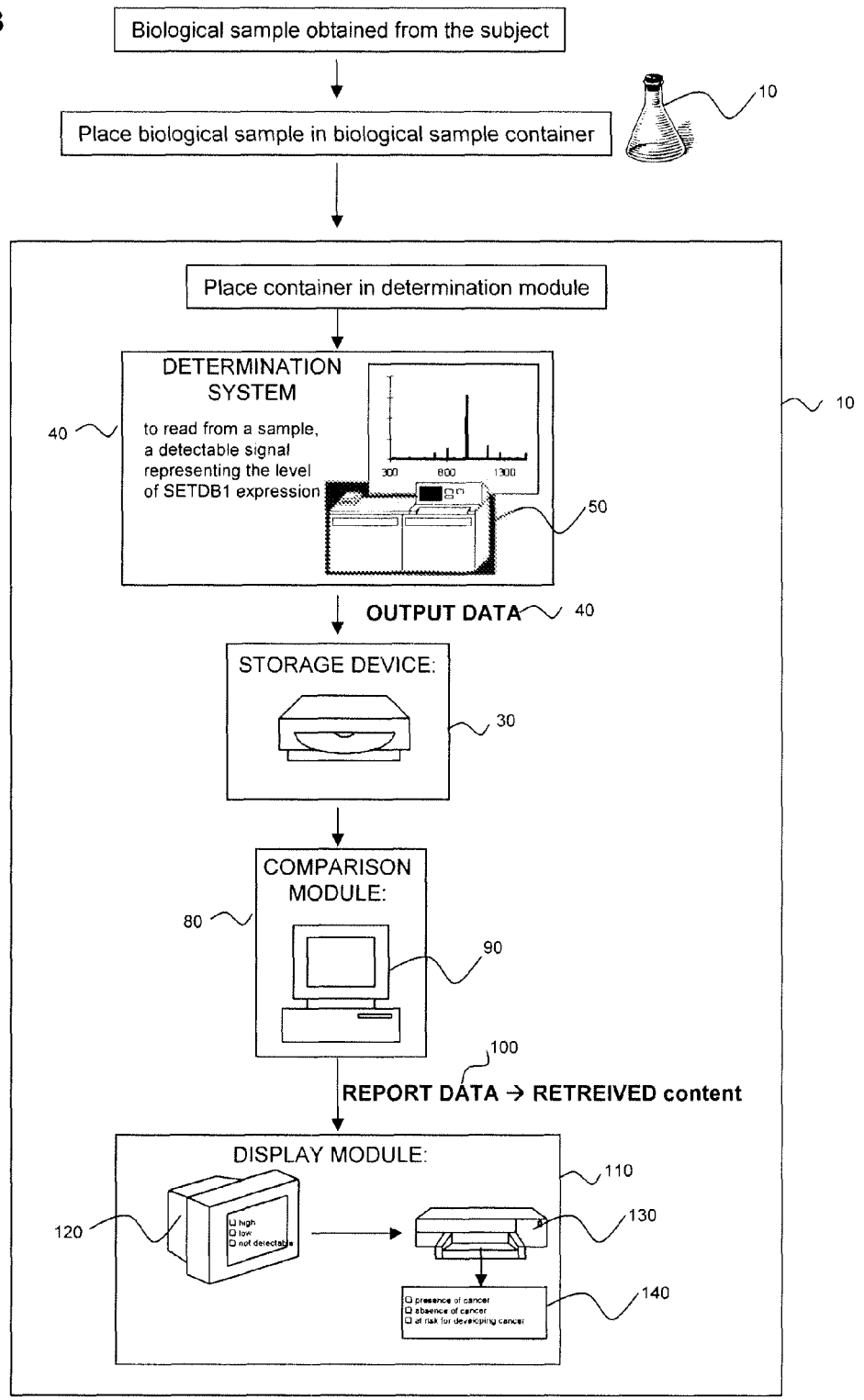

FIG. 13 is a block diagram depicting an exemplary system for use with the diagnostic methods described herein.

Figure 14:
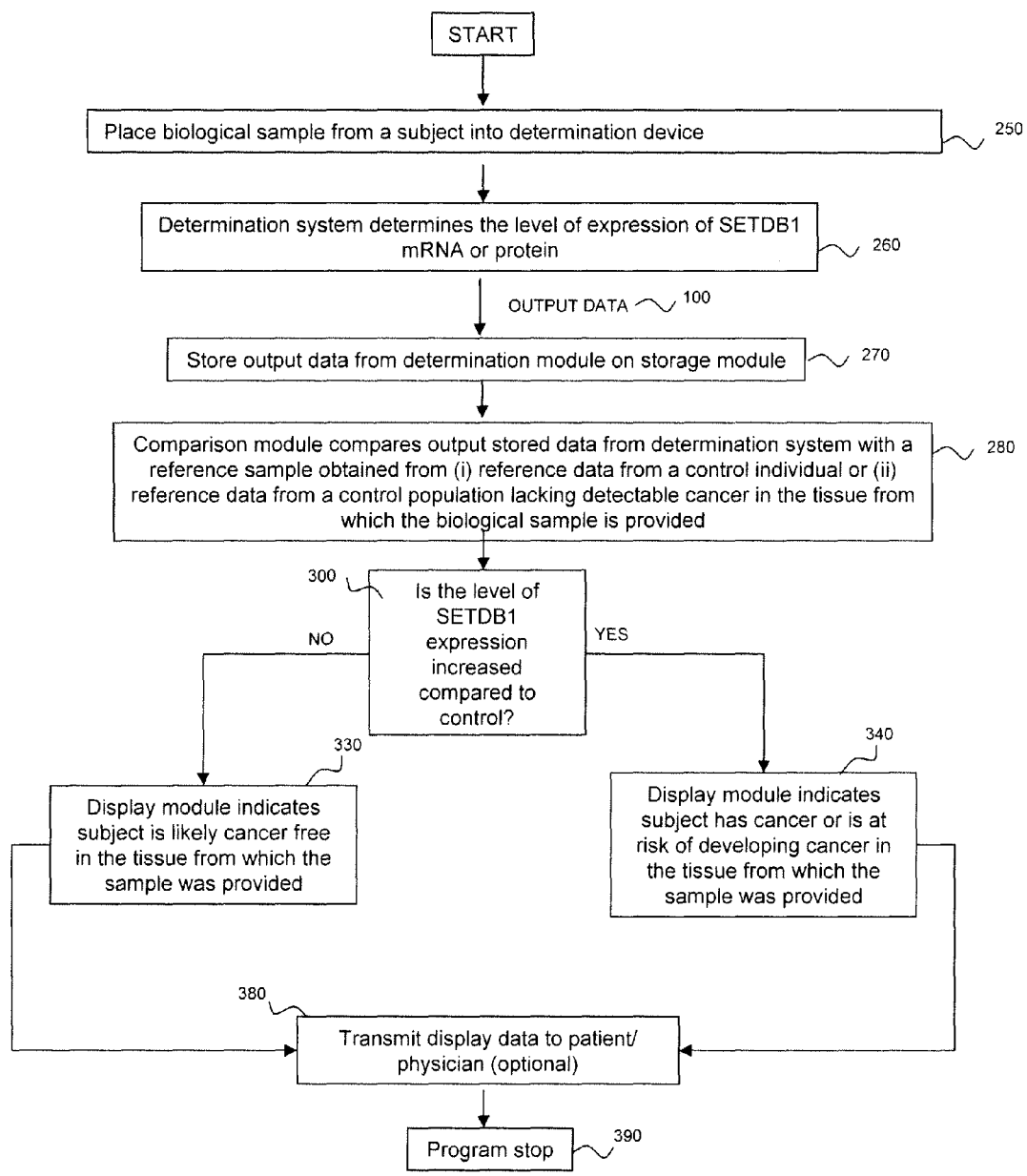

FIG. 14 is a block diagram depicting exemplary instructions encoded on a computer readable storage medium for use with the systems described herein.

DETAILED DESCRIPTION

The methods described herein relate to the diagnosis of cancer by measuring the level of SETDB1 in a biological sample from a subject suspected of having cancer. Also described herein are methods for treating cancer by administering an inhibitor of SETDB1 to a subject having cancer (e.g., melanoma).

Cancer

Essentially any type of cancer having SETDB1 expression levels at least 10% higher than that of a subject substantially free of cancer can be diagnosed and/or treated with the methods described herein. In one embodiment, the cancer comprises a solid tumor or growth. In one embodiment, the cancer is melanoma. Alternatively, in other embodiments the cancer is thyroid cancer, pancreas or lung cancer.

Obtaining a Biological Sample

A biological sample can be obtained from essentially any tissue suspected of containing cancerous cells. Some non-limiting examples of tissues include e.g., brain, liver, lung, gut, stomach, fat, muscle, spleen, testes, uterus, ovary, skin, endocrine organ and bone, etc. In one embodiment, a biological sample comprises cells including, but not limited to, epithelial, endothelial, neuronal, adipose, cardiac, skeletal muscle, fibroblast, immune cells, hepatic, splenic, lung, circulating blood cells, reproductive cells, gastrointestinal, renal, bone marrow, and pancreatic cells. In one embodiment, the biological sample is a biopsy from a growth or tumor.

In one embodiment, the biological sample is a skin sample from an abnormal skin lesion (e.g., suspected melanoma). A skin lesion or mole is considered to be abnormal if it has one or more of the following characteristics: (i) change in an existing mole, (ii) assymetrical shape, (ii) irregular border, (iii) color changes, (iv) diameter greater than ¼ of an inch, and (v) evolving characteristics. One of skill in the art can identify a skin lesion that may indicate the presence of melanoma, which can be confirmed and/or treated with the methods described herein.

Samples can be obtained by any method to one of skill in the art including e.g., needle biopsy, fine needle aspiration, core needle biopsy, vacuum assisted biopsy, open surgical biopsy, among others.

REFERENCES OR REFERENCE SAMPLES

As used herein, the terms "reference sample" and "reference" refer to the level of SETDB1 expression, as that term is used herein, in a known sample against which another sample is compared (i.e., obtained from a subject substantially free of cancer). A standard is useful for determining the amount of SETDB1 or the relative increase/decrease of SETDB1 in a biological sample. A standard serves as a reference level for comparison, such that samples can be normalized to an appropriate standard in order to infer the presence, absence or extent of cancer in a subject.

In one embodiment, a biological standard is obtained at an earlier time point (presumably prior to the onset of cancer) from the same individual that is to be tested or treated as described herein. Alternatively, a standard can be from the same individual having been taken at a time after the onset or diagnosis of cancer. In such instances, the standard can provide a measure of the efficacy of treatment.

A standard level can be obtained, for example, from a known biological sample from a different individual (e.g., not the individual being tested) that is substantially free of cancer. A known sample can also be obtained by pooling samples from a plurality of individuals to produce a standard over an averaged population, wherein a standard represents an average level of SETDB1 among a population of individuals. Thus, the level of SETDB1 in a standard obtained in this manner is representative of an average level of this marker in a general population or a diseased population. An individual sample is compared to this population standard by comparing expression of SETDB1 from a sample relative to the population standard. Generally, an increase in the amount of SETDB1 over a standard (e.g., obtained from subjects substantially free of cancer) will indicate the presence of cancer, while a decrease in the amount of SETDB1 will indicate no cancer is present. The converse is contemplated in cases where a standard is obtained from a population of subjects having cancer. It should be noted that there is often variability among individuals in a population, such that some individuals will have higher levels of SETDB1 expression, while other individuals have lower levels of expression. However, one skilled in the art can make logical inferences on an individual basis regarding the detection and treatment of cancer as described herein.

A standard or series of standards can also be synthesized. A known amount of SETDB1 (or a series of known amounts) can be prepared within the typical expression range for SETDB1 that is observed in a general population. This method has an advantage of being able to compare the extent of disease in two individuals in a mixed population. This method can also be useful for subjects who lack a prior sample to act as a standard or for routine follow-up post-diagnosis. This type of method can also allow standardized tests to be performed among several clinics, institutions, or countries etc.

Detection of SETDB1

SETDB1 can be detected by any means of detecting expression of a polypeptide, or fragment thereof, or an mRNA transcript of the polypeptide. These detection methods are known to those skilled in the art and/or are described briefly below. In one embodiment, the level of SETDB1 can be normalized to another protein (i.e., a normalizing protein) such as e.g., a housekeeping gene or another gene determined to lack significant variations in level/concentration among samples or among disease states. Normalizing proteins and their use are known to those of skill in the art.

Protein Expression Level

Protein from a biological sample to be analyzed can be detected or isolated using techniques which are well known to one of skill in the art, including but not limited to immunohistochemistry, Western blot analysis, (i.e.), immunoblotting, ELISA, immunoprecipitation, lateral flow immunoassay, radioimmunoas say, etc. Antibodies directed against SETDB1 can be applied for disease diagnostics and prognostics. Such diagnostic methods can be used to detect abnormalities in the level of expression of SETDB1, and/or the tissue, cellular, or subcellular location of the peptide. Generally, however, it will be the amount of SETDB1 that is of primary interest. Antibodies to be used for protein analysis are widely available through commercial sources including AbCam (Cambridge, Mass.), New England Biolabs (Ipswich, Mass.), Santa Cruz Biotechnologies (Santa Cruz, Calif.), and Cell Signaling (Danvers, Mass.), among others.

Antibodies can also be raised against a polypeptide or portion of a polypeptide by methods known to those skilled in the art. Antibodies are readily raised in animals such as rabbits or mice by immunization with the gene product, or a fragment thereof. Immunized mice are particularly useful for providing sources of B cells for the manufacture of hybridomas, which in turn are cultured to produce large quantities of monoclonal antibodies. While both polyclonal and monoclonal antibodies can be used in the methods described herein, it is preferred that a monoclonal antibody is used where conditions require increased specificity for a particular protein. Antibody manufacture methods are described herein, for example, in Harlow et al., 1988. The antibodies that recognize SETDB1 may be any antibody variant, antibody derivative, bispecific molecule, human antibody, humanized antibody, monoclonal antibody, human monoclonal, and variants and antigen-binding fragments thereof. Conventional methods for immunohistochemistry are described in Harlow and Lane, 1988 and Ausbel et al, 1987.

Transcript Expression Level

In an alternative embodiment, expression levels of SETDB1 can be determined by measuring the level of messenger RNA (mRNA) expression. Detection of mRNA expression is known by persons skilled in the art, and can comprise, for example PCR procedures, RT-PCR, Northern blot analysis, RNAse protection assay, etc. Nucleic acid and ribonucleic acid (RNA) molecules can be isolated from a particular biological sample using any of a number of procedures that are well-known in the art, the particular isolation procedure chosen being appropriate for the particular biological sample.

In general, PCR provides a method of gene amplification which is comprised of (i) sequence-specific hybridization of primers to specific genes within a nucleic acid sample or library, (ii) subsequent amplification involving multiple rounds of annealing, elongation, and denaturation using a DNA polymerase, and (iii) screening the PCR products for an amplified product of the correct size. The primers used are oligonucleotides of sufficient length and appropriate sequence to provide initiation of polymerization, i.e. each primer is specifically designed to be complementary to one strand of the genomic locus to be amplified.

SETDB1 expression levels can be determined by reverse-transcription (RT) PCR and by quantitative RT-PCR (QRT-PCR) or real-time RT-PCR methods. Methods of RT-PCR and QRT-PCR are well known in the art, and are described in more detail below. In one embodiment, labeled probes can be used in conjunction with amplification of cDNA. (Holland et al., 1991). U.S. Pat. No. 5,210,015 by Gelfand et al. describes fluorescence-based approaches to provide real time measurements of amplification products during PCR. Such approaches have generally either employed intercalating dyes (such as ethidium bromide) to indicate the amount of double-stranded DNA present, or they have employed probes containing fluorescence-quencher pairs (also referred to as the "Taq-Man" approach) where the probe is cleaved during amplification to release a fluorescent molecule whose concentration is proportional to the amount of double-stranded DNA present. During amplification, the probe is digested by the nuclease activity of a polymerase when hybridized to the target sequence to cause the fluorescent molecule to be separated from the quencher molecule, thereby causing fluorescence from the reporter molecule to appear. The Taq-Man approach uses a probe containing a reporter molecule-quencher molecule pair that specifically anneals to a region of a target polynucleotide.

Primers or probes of use in the methods described herein include naturally occurring or recombinant single- or double-stranded nucleic acids or chemically synthesized nucleic acids. They may be labeled by nick translation, Klenow fill-in reaction, PCR or other methods known in the art. Probes useful in the method described herein, their preparation and/ or labeling are described in, for example Sambrook et al. (1989). A probe can be a polynucleotide of any length suitable for selective hybridization to a nucleic acid containing a polymorphic region of the invention. Length of the probe used will depend, in part, on the nature of the assay used and the hybridization conditions employed. In one embodiment, probes are labeled with two fluorescent dye molecules to form so-called "molecular beacons" (Tyagi, S. and Kramer, F. R., 1996). Such molecular beacons signal binding to a complementary nucleic acid sequence through relief of intramolecular fluorescence quenching between dyes bound to opposing ends on an oligonucleotide probe. A quenching molecule is useful with a particular fluorophore if it has sufficient spectral overlap to substantially inhibit fluorescence of the fluorophore when the two are held proximal to one another, such as in a molecular beacon, or when attached to the ends of an oligonucleotide probe from about 1 to about 25 nucleotides.

In some embodiments, primers for use in the methods of the invention are nucleic acids which hybridize to a nucleic acid sequence which is adjacent to the region of interest or which covers the region of interest and is extended. A primer can be used alone in a detection method, or a primer can be used together with at least one other primer or probe in a detection method. Primers can also be used to amplify at least a portion of a nucleic acid. In some embodiments probes for use in the methods are nucleic acids which hybridize to the region of interest and which are not further extended. The nucleic acids, or fragments thereof, to be used in the methods of the invention can be prepared according to methods known in the art and described, e.g., in Sambrook et al. (1989), supra. For example, discrete fragments of the DNA can be prepared and cloned using restriction enzymes. Alternatively, discrete fragments can be prepared using the Polymerase Chain Reaction (PCR) using primers having an appropriate sequence under the manufacturer's conditions, (described above). Oligonucleotides can be synthesized by standard methods known in the art, e.g. by use of an automated DNA synthesizer (such as are commercially available from Biosearch, Applied Biosystems, etc.). As examples, phosphorothioate oligonucleotides can be synthesized by the method of Stein et al., 1988, methylphosphonate oligonucleotides can be prepared by use of controlled pore glass polymer supports (Sarin et al., 1988). Reagents and hardware for conducting PCR are commercially available. Primers useful to amplify sequences from a particular gene region are preferably complementary to, and hybridize specifically to sequences in the target region or in its flanking regions. Nucleic acid sequences generated by amplification may be sequenced directly.

Anti-Cancer Agents and SETDB1 Inhibitors

Essentially any agent that inhibits or reduces the growth of a tumor or the activity of SETDB1 can be used for treating a subject identified using the methods described herein. An agent can be e.g., a small molecule, a nucleic acid, an RNA interference molecule, a peptide, a protein, or an antibody, among others.

Small Molecule Inhibitors

As used herein, the term "small molecule" refers to a chemical agent including, but not limited to, peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

Small molecules agents can be identified from within a small molecule library, which can be obtained from commercial sources such as AMRI (Albany, N.Y.), AsisChem Inc. (Cambridge, Mass.), TimTec (Newark, Del.), among others, or from libraries as known in the art.

Antibodies

Antibodies can be used to inhibit tumor growth by e.g., recognition of an epitope such that a bound antibody inhibits cell growth, proliferation or tumor growth by e.g., a target enzyme or SETDB1. Production of antibodies useful for the methods described herein are known to those of skill in the art and are described in e.g., Harlow & Lane, Antibodies, A Laboratory Manual (CSHP NY, 1988, which is herein incorporated by reference in its entirety).

RNA Interference

RNA interference agents can be used with the methods described herein, to inhibit the growth of a tumor or SETDB1 activity in a tissue. "RNA interference (RNAi)" is an evolutionarily conserved process whereby the expression or introduction of RNA of a sequence that is identical or highly similar to a target gene results in the sequence specific degradation or specific post-transcriptional gene silencing (PTGS) of messenger RNA (mRNA) transcribed from that targeted gene (see Coburn, G. and Cullen, B., J. of Virology 76(18):9225 (2002), herein incorporated by reference in its entirety), thereby inhibiting expression of the target gene.

As used herein, "inhibition of target gene expression" includes any decrease in expression or protein activity or level of the target gene or protein encoded by the target gene as compared to a situation wherein no RNA interference has been induced. The decrease can be of at least 20%, 30%, 40%, 50%, 60%, 70%, 80%, 90%, 95% or 99% or more as compared to the expression of a target gene or the activity or level of the protein encoded by a target gene which has not been targeted by an RNA interfering agent. RNA interfering agents contemplated for use with the methods described herein include, but are not limited to, siRNA, shRNA, miRNA, and dsRNAi.

In general, any method of delivering a nucleic acid molecule can be adapted for use with an RNAi interference molecule (see e.g., Akhtar S. and Julian R L. (1992) Trends Cell. Biol. 2(5):139-144; WO94/02595, which are incorporated herein by reference in their entirety). The non-specific effects of an RNAi molecule can be minimized by local administration by e.g., direct injection into a tissue including, for example, a tumor or topically administering the molecule. Local administration of an RNAi molecule to a tumor limits the exposure of the e.g., siRNA to systemic tissues and permits a lower dose of the RNAi molecule to be administered.

For administering an RNAi molecule systemically for the treatment of a disease, the RNAi molecule can be either be modified or alternatively delivered using a drug delivery system; both methods act to prevent the rapid degradation of the RNAi molecule by endo- and exo-nucleases in vivo. Modification of the RNAi molecule or the pharmaceutical carrier can also permit targeting of the RNAi molecule to the target tissue and avoid undesirable off-target effects.

In an alternative embodiment, the RNAi molecules can be delivered using drug delivery systems such as e.g., a nanoparticle, a dendrimer, a polymer, liposomes, or a cationic delivery system. Positively charged cationic delivery systems facilitate binding of an RNA interference molecule (negatively charged) and also enhance interactions at the negatively charged cell membrane to permit efficient uptake of an siRNA by the cell. Cationic lipids, dendrimers, or polymers can either be bound to an RNA interference molecule, or induced to form a vesicle or micelle (see e.g., Kim S H., et al (2008) Journal of Controlled Release 129(2):107-116) that encases an RNAi molecule. The formation of vesicles or micelles further prevents degradation of the RNAi molecule when administered systemically. Methods for making and administering cationic-RNAi complexes are well within the abilities of one skilled in the art (see e.g., Sorensen, D R., et al (2003) J. Mol. Biol 327:761-766; Verma, U N., et al (2003) Clin. Cancer Res. 9:1291-1300; Arnold, A S et al (2007) J. Hypertens. 25:197-205, which are incorporated herein by reference in their entirety).

Some non-limiting examples of drug delivery systems useful for systemic administration of RNAi include DOTAP (Sorensen, D R., et al (2003), supra; Verma, U N., et al (2003), supra), Oligofectamine, "solid nucleic acid lipid particles" (Zimmermann, T S., et al (2006) Nature 441:111-114), cardiolipin (Chien, P Y., et al (2005) Cancer Gene Ther. 12:321-328; Pal, A., et al (2005) Int J. Oncol. 26:1087-1091), polyethyleneimine (Bonnet M E., et al (2008) Pharm. Res. August 16 Epub ahead of print; Aigner, A. (2006) J. Biomed. Biotechnol. 71659), Arg-Gly-Asp (RGD) peptides (Liu, S. (2006) Mol. Pharm. 3:472-487), and polyamidoamines (Tomalia, D A., et al (2007) Biochem. Soc. Trans. 35:61-67; Yoo, H., et al (1999) Pharm. Res. 16:1799-1804). In some embodiments, an RNAi molecule forms a complex with cyclodextrin for systemic administration. Methods for administration and pharmaceutical compositions of RNAi molecules and cyclodextrins can be found in U.S. Pat. No. 7,427,605, which is herein incorporated by reference in its entirety. Specific methods for administering an RNAi molecule for the inhibition of angiogenesis can be found in e.g., U.S. Patent Application No. 20080152654, which is herein incorporated by reference in its entirety.

Dosage and Administration

In one aspect, the methods described herein provide a method for treating cancer (e.g., melanoma) in a subject. In one embodiment, the subject can be a mammal. In another embodiment, the mammal can be a human, although the approach is effective with respect to all mammals. The method comprises administering to the subject an effective amount of a pharmaceutical composition comprising an agent that inhibits SETDB1, in a pharmaceutically acceptable carrier. In one embodiment, the agent comprises mithramycin or a derivative thereof.

The dosage range for the agent depends upon the potency, and include amounts large enough to produce the desired effect, e.g., a reduction in SETDB1 activity. The dosage should not be so large as to cause unacceptable adverse side effects. Generally, the dosage will vary with the type of inhibitor (e.g., an antibody or fragment, small molecule, siRNA, etc.), and with the age, condition, and sex of the patient. The dosage can be determined by one of skill in the art and can also be adjusted by the individual physician in the event of any complication. Typically, the dosage ranges from 0.001 mg/kg body weight to 5 g/kg body weight. In some embodiments, the dosage range is from 0.001 mg/kg body weight to 1 g/kg body weight, from 0.001 mg/kg body weight to 0.5 g/kg body weight, from 0.001 mg/kg body weight to 0.1 g/kg body weight, from 0.001 mg/kg body weight to 50 mg/kg body weight, from 0.001 mg/kg body weight to 25 mg/kg body weight, from 0.001 mg/kg body weight to 10 mg/kg body weight, from 0.001 mg/kg body weight to 5 mg/kg body weight, from 0.001 mg/kg body weight to 1 mg/kg body weight, from 0.001 mg/kg body weight to 0.1 mg/kg body weight, from 0.001 mg/kg body weight to 0.005 mg/kg body weight. Alternatively, in some embodiments the dosage range is from 0.1 g/kg body weight to 5 g/kg body weight, from 0.5 g/kg body weight to 5 g/kg body weight, from 1 g/kg body weight to 5 g/kg body weight, from 1.5 g/kg body weight to 5 g/kg body weight, from 2 g/kg body weight to 5 g/kg body weight, from 2.5 g/kg body weight to 5 g/kg body weight, from 3 g/kg body weight to 5 g/kg body weight, from 3.5 g/kg body weight to 5 g/kg body weight, from 4 g/kg body weight to 5 g/kg body weight, from 4.5 g/kg body weight to 5 g/kg body weight, from 4.8 g/kg body weight to 5 g/kg body weight. In one embodiment, the dose range is from 5 μg/kg body weight to 30 μg/kg body weight. Alternatively, the dose range will be titrated to maintain serum levels between 5 μg/mL and 30 μg/mL.

Administration of the doses recited above can be repeated for a limited period of time. In some embodiments, the doses are given once a day, or multiple times a day, for example but not limited to three times a day. In a preferred embodiment, the doses recited above are administered daily for several weeks or months. The duration of treatment depends upon the subject's clinical progress and responsiveness to therapy. Continuous, relatively low maintenance doses are contemplated after an initial higher therapeutic dose.

A therapeutically effective amount is an amount of an agent that is sufficient to produce a statistically significant, measurable change in SETDB1 activity or tumor growth/size (see "Efficacy Measurement" below). Such effective amounts can be gauged in clinical trials as well as animal studies for a given agent.

Agents useful in the methods and compositions described herein can be administered topically, intravenously (by bolus or continuous infusion), orally, by inhalation, intraperitoneally, intramuscularly, subcutaneously, intracavity, and can be delivered by peristaltic means, if desired, or by other means known by those skilled in the art. In one embodiment it is preferred that the agents for the methods described herein are administered directly to the tumor (e.g., during surgery or by direct injection). The agent can be administered systemically, if so desired.

Therapeutic compositions containing at least one agent can be conventionally administered in a unit dose. The term "unit dose" when used in reference to a therapeutic composition refers to physically discrete units suitable as unitary dosage for the subject, each unit containing a predetermined quantity of active material calculated to produce the desired therapeutic effect in association with the required physiologically acceptable diluent, i.e., carrier, or vehicle.

The compositions are administered in a manner compatible with the dosage formulation, and in a therapeutically effective amount. The quantity to be administered and timing depends on the subject to be treated, capacity of the subject's system to utilize the active ingredient, and degree of therapeutic effect desired. An agent can be targeted by means of a targeting moiety, such as e.g., an antibody or targeted liposome technology. In some embodiments, an agent can be targeted to a tissue by using bispecific antibodies, for example produced by chemical linkage of an anti-ligand antibody (Ab) and an Ab directed toward a specific target. To avoid the limitations of chemical conjugates, molecular conjugates of antibodies can be used for production of recombinant bispecific single-chain Abs directing ligands and/or chimeric inhibitors at cell surface molecules. The addition of an antibody to an agent permits the agent to accumulate additively at the desired target site (e.g., tumor or lesion). Antibody-based or non-antibody-based targeting moieties can be employed to deliver a ligand or the inhibitor to a target site. Preferably, a natural binding agent for an unregulated or disease associated antigen is used for this purpose.

Precise amounts of active ingredient required to be administered depend on the judgment of the practitioner and are particular to each individual. However, suitable dosage ranges for systemic application are disclosed herein and depend on the route of administration. Suitable regimes for administration are also variable, but are typified by an initial administration followed by repeated doses at one or more intervals by a subsequent injection or other administration. Alternatively, continuous intravenous infusion sufficient to maintain concentrations in the blood in the ranges specified for in vivo therapies are contemplated.

Pharmaceutical Compositions

The present invention involves therapeutic compositions useful for practicing the therapeutic methods described herein. Therapeutic compositions contain a physiologically tolerable carrier together with an active agent as described herein, dissolved or dispersed therein as an active ingredient. In a preferred embodiment, the therapeutic composition is not immunogenic when administered to a mammal or human patient for therapeutic purposes. As used herein, the terms "pharmaceutically acceptable", "physiologically tolerable" and grammatical variations thereof, as they refer to compositions, carriers, diluents and reagents, are used interchangeably and represent that the materials are capable of administration to or upon a mammal without the production of undesirable physiological effects such as nausea, dizziness, gastric upset and the like. A pharmaceutically acceptable carrier will not promote the raising of an immune response to an agent with which it is admixed, unless so desired. The preparation of a pharmacological composition that contains active ingredients dissolved or dispersed therein is well understood in the art and need not be limited based on formulation. Typically such compositions are prepared as injectable either as liquid solutions or suspensions, however, solid forms suitable for solution, or suspensions, in liquid prior to use can also be prepared. The preparation can also be emulsified or presented as a liposome composition. The active ingredient can be mixed with excipients which are pharmaceutically acceptable and compatible with the active ingredient and in amounts suitable for use in the therapeutic methods described herein. Pharmaceutical compositions having active RNAi ingredients in a preparation are contemplated for delivery as described herein above, or in references cited and incorporated herein in that section. Suitable excipients include, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient. The therapeutic composition of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like. Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active agent used in the methods described herein that will be effective in the treatment of a particular disorder or condition will depend on the nature of the disorder or condition, and can be determined by standard clinical techniques.

Efficacy Measurement

The efficacy of a given treatment for cancer (e.g., melanoma (can be determined by the skilled clinician. However, a treatment is considered "effective treatment," as the term is used herein, if any one or all of the signs or symptoms of cancer are altered in a beneficial manner, other clinically accepted symptoms or markers of disease are improved, or even ameliorated, e.g., by at least 10% following treatment with an agent that inhibits SETDB1 levels. Efficacy can also be measured by a failure of an individual to worsen as assessed by stabilization of tumor growth, hospitalization or need for medical interventions (i.e., progression of the disease is halted or at least slowed). Methods of measuring these indicators are known to those of skill in the art and/or described herein. Treatment includes any treatment of a disease in an individual or an animal (some non-limiting examples include a human, or a mammal) and includes: (1) inhibiting the disease, e.g., arresting, or slowing tumor or lesion growth; or (2) relieving the disease, e.g., causing regression of symptoms, reducing tumor or lesion size; and (3) preventing or reducing the likelihood of the development of cancer (e.g., melanoma), or preventing metastasis of cancer.

An effective amount for the treatment of a disease means that amount which, when administered to a mammal in need thereof, is sufficient to result in effective treatment as that term is defined herein, for that disease. Efficacy of an agent can be determined by assessing physical indicators of cancer (e.g., melanoma), such as e.g., tumor size or lesion size, metastasis, tumor growth rate, etc.

Systems

Embodiments of the invention also provide for systems (and computer readable media for causing computer systems) to perform a method for diagnosing cancer in a subject, or assessing a subject's risk of developing cancer.

Embodiments of the invention can be described through functional modules, which are defined by computer executable instructions recorded on computer readable media and which cause a computer to perform method steps when executed. The modules are segregated by function for the sake of clarity. However, it should be understood that the modules/systems need not correspond to discreet blocks of code and the described functions can be carried out by the execution of various code portions stored on various media and executed at various times. Furthermore, it should be appreciated that the modules may perform other functions, thus the modules are not limited to having any particular functions or set of functions.

The computer readable storage media #30 can be any available tangible media that can be accessed by a computer. Computer readable storage media includes volatile and non-volatile, removable and non-removable tangible media implemented in any method or technology for storage of information such as computer readable instructions, data structures, program modules or other data. Computer readable storage media includes, but is not limited to, RAM (random access memory), ROM (read only memory), EPROM (eraseable programmable read only memory), EEPROM (electrically eraseable programmable read only memory), flash memory or other memory technology, CD-ROM (compact disc read only memory), DVDs (digital versatile disks) or other optical storage media, magnetic cassettes, magnetic tape, magnetic disk storage or other magnetic storage media, other types of volatile and non-volatile memory, and any other tangible medium which can be used to store the desired information and which can accessed by a computer including and any suitable combination of the foregoing.

Computer-readable data embodied on one or more computer-readable storage media may define instructions, for example, as part of one or more programs, that, as a result of being executed by a computer, instruct the computer to perform one or more of the functions described herein, and/or various embodiments, variations and combinations thereof. Such instructions may be written in any of a plurality of programming languages, for example, Java, J#, Visual Basic, C, C#, C++, Fortran, Pascal, Eiffel, Basic, COBOL assembly language, and the like, or any of a variety of combinations thereof. The computer-readable storage media on which such instructions are embodied may reside on one or more of the components of either of a system, or a computer readable storage medium described herein, may be distributed across one or more of such components.

The computer-readable storage media may be transportable such that the instructions stored thereon can be loaded onto any computer resource to implement the aspects of the present invention discussed herein. In addition, it should be appreciated that the instructions stored on the computer-readable medium, described above, are not limited to instructions embodied as part of an application program running on a host computer. Rather, the instructions may be embodied as any type of computer code (e.g., software or microcode) that can be employed to program a computer to implement aspects of the present invention. The computer executable instructions may be written in a suitable computer language or combination of several languages. Basic computational biology methods are known to those of ordinary skill in the art and are described in, for example, Setubal and Meidanis et al., Introduction to Computational Biology Methods (PWS Publishing Company, Boston, 1997); Salzberg, Searles, Kasif, (Ed.), Computational Methods in Molecular Biology, (Elsevier, Amsterdam, 1998); Rashidi and Buehler, Bioinformatics Basics: Application in Biological Science and Medicine (CRC Press, London, 2000) and Ouelette and Bzevanis Bioinformatics: A Practical Guide for Analysis of Gene and Proteins (Wiley & Sons, Inc., 2nd ed., 2001).

The functional modules of certain embodiments of the invention include at minimum a determination system #40, a storage device #30, a comparison module #80, and a display module #110. The functional modules can be executed on one, or multiple, computers, or by using one, or multiple, computer networks. The determination system has computer executable instructions to provide e.g., expression information in computer readable form.

The determination system #40, can comprise any system for detecting a signal representing the expression of SETDB1. Such systems can include microscope data acquisition system, RNA expression arrays, RT-PCR etc.

The information determined in the determination system can be read by the storage device #30. As used herein the "storage device" is intended to include any suitable computing or processing apparatus or other device configured or adapted for storing data or information. Examples of electronic apparatus suitable for use with the present invention include stand-alone computing apparatus, data telecommunications networks, including local area networks (LAN), wide area networks (WAN), Internet, Intranet, and Extranet, and local and distributed computer processing systems. Storage devices also include, but are not limited to: magnetic storage media, such as floppy discs, hard disc storage media, magnetic tape, optical storage media such as CD-ROM, DVD, electronic storage media such as RAM, ROM, EPROM, EEPROM and the like, general hard disks and hybrids of these categories such as magnetic/optical storage media. The storage device is adapted or configured for having recorded thereon values representing expression levels of SETDB1 information. Such information may be provided in digital form that can be transmitted and read electronically, e.g., via the Internet, on diskette, via USB (universal serial bus) or via any other suitable mode of communication.

As used herein, "stored" refers to a process for encoding information on the storage device. Those skilled in the art can readily adopt any of the presently known methods for recording information on known media to generate manufactures comprising expression information.

In one embodiment the reference data stored in the storage device to be read by the comparison module is e.g., expression data obtained from a population of subjects that are substantially free of cancer.

The "comparison module" #80 can use a variety of available software programs and formats for the comparison operative to compare sequence information data determined in the determination system to reference samples and/or stored reference data. In one embodiment, the comparison module is configured to use pattern recognition techniques to compare information from one or more entries to one or more reference data patterns. The comparison module may be configured using existing commercially-available or freely-available software for comparing patterns, and may be optimized for particular data comparisons that are conducted. The comparison module provides computer readable information related to the expression of SETDB1 in a subject.

The comparison module, or any other module of the invention, may include an operating system (e.g., UNIX) on which runs a relational database management system, a World Wide Web application, and a World Wide Web server. World Wide Web application includes the executable code necessary for generation of database language statements (e.g., Structured Query Language (SQL) statements). Generally, the executables will include embedded SQL statements. In addition, the World Wide Web application may include a configuration file which contains pointers and addresses to the various software entities that comprise the server as well as the various external and internal databases which must be accessed to service user requests. The Configuration file also directs requests for server resources to the appropriate hardware—as may be necessary should the server be distributed over two or more separate computers. In one embodiment, the World Wide Web server supports a TCP/IP protocol. Local networks such as this are sometimes referred to as "Intranets." An advantage of such Intranets is that they allow easy communication with public domain databases residing on the World Wide Web (e.g., the GenBank or Swiss Pro World Wide Web site). Thus, in a particular preferred embodiment of the present invention, users can directly access data (via Hypertext links for example) residing on Internet databases using a HTML interface provided by Web browsers and Web servers.

The comparison module provides a computer readable comparison result that can be processed in computer readable form by predefined criteria, or criteria defined by a user, to provide a content based in part on the comparison result that may be stored and output as requested by a user using a display module #110.

The content based on the comparison result, may be the expression of SETDB1 indicating the presence of cancer in a subject. Alternatively, the content based on the comparison result may be the absence of expression of SETDB1 indicating the absence of cancer in an individual.

In one embodiment of the invention, the content based on the comparison result is displayed on a computer monitor #120. In one embodiment of the invention, the content based on the comparison result is displayed through printable media #130, #140. The display module can be any suitable device configured to receive from a computer and display computer readable information to a user. Non-limiting examples include, for example, general-purpose computers such as those based on Intel PENTIUM-type processor, Motorola PowerPC, Sun UltraSPARC, Hewlett-Packard PA-RISC processors, any of a variety of processors available from Advanced Micro Devices (AMD) of Sunnyvale, Calif., or any other type of processor, visual display devices such as flat panel displays, cathode ray tubes and the like, as well as computer printers of various types.

In one embodiment, a World Wide Web browser is used for providing a user interface for display of the content based on the comparison result. It should be understood that other modules of the invention can be adapted to have a web browser interface. Through the Web browser, a user may construct requests for retrieving data from the comparison module. Thus, the user will typically point and click to user interface elements such as buttons, pull down menus, scroll bars and the like conventionally employed in graphical user interfaces.

The methods described herein therefore provide for systems (and computer readable media for causing computer systems) to perform methods for diagnosing cancer or assessing risk for developing such a disorder in a subject.

Systems and computer readable media described herein are merely illustrative embodiments of the invention for performing methods of diagnosis in an individual, and are not intended to limit the scope of the invention. Variations of the systems and computer readable media described herein are possible and are intended to fall within the scope of the invention.

The modules of the machine, or those used in the computer readable medium, may assume numerous configurations. For example, function may be provided on a single machine or distributed over multiple machines.

It is understood that the foregoing description and the following examples are illustrative only and are not to be taken as limitations upon the scope of the invention. Various changes and modifications to the disclosed embodiments, which will be apparent to those of skill in the art, may be made without departing from the spirit and scope of the present invention. Further, all patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and do not constitute any admission as to the correctness of the dates or contents of these documents.

The present invention may be as defined in any one of the following numbered paragraphs.

1. A method for facilitating the diagnosis of cancer in a subject, the method comprising: measuring the level of SETDB1 in a biological sample obtained from a subject, wherein an increase in the SETDB1 level in the sample compared to a reference is indicative of cancer in the subject.
2. The method of paragraph 1, wherein the cancer comprises a solid tumor or growth.
3. The method of paragraph 1 or 2, wherein the cancer is selected from the group consisting of: melanoma, thyroid, pancreas and lung cancer.
4. The method of paragraph 1, 2 or 3, wherein the growth comprises a nevi.
5. The method of any one of the preceding paragraphs, wherein the tumor or growth comprises a melanocyte.
6. The method of any one of the preceding paragraphs, wherein the subject is a mammal.
7. The method of any one of the preceding paragraphs, wherein the subject is a human.
8. The method of any one of the preceding paragraphs, wherein the level of SETDB1 is detected at the mRNA level or the protein level.
9. The method of any one of the preceding paragraphs, wherein the level of SETDB1 is detected using an antibody-based binding agent which specifically binds to SETDB1 protein.
10. The method of any one of the preceding paragraphs, further comprising administering to the subject at least one anti-cancer agent.
11. The method of any one of the preceding paragraphs, further comprising measuring the expression level of at least one additional cancer marker.
12. The method of any one of the preceding paragraphs, wherein the at least one additional cancer marker is p53 or BRAF.
13. The method of any one of the preceding paragraphs, wherein the BRAF comprises an activating mutation.
14. The method of any one of the preceding paragraphs, wherein the activating mutation comprises $BRAF^{V600E}$.
15. A method for treating cancer in a subject, the method comprising administering an inhibitor of SETDB1 to a subject having or suspected of having cancer.
16. The method of paragraph 15, wherein the subject is a mammal.

17. The method of paragraph 15 or 16, wherein the subject is human.
18. The method of any one of the paragraphs 15-17, further comprising a step of selecting a subject having cancer.
19. The method of any one of the paragraphs 15-18, wherein the selecting step comprises comparing the level of SETDB1 in a sample obtained from a subject to a reference, wherein an increase in SETDB1 level in the sample compared to the reference is indicative of cancer in the subject.
20. The method of any one of the paragraphs 15-19, wherein the cancer comprises a solid tumor or growth.
21. The method of any one of the paragraphs 15-20, wherein the growth comprises a nevi.
22. The method of any one of the paragraphs 15-21, wherein the tumor or growth comprises a melanocyte.
23. The method of any one of the paragraphs 15-22, wherein the cancer is selected from the group consisting of: melanoma, thyroid, pancreas and lung cancer.
24. The method of any one of the paragraphs 15-23, wherein the level of SETDB1 is detected at the mRNA level or the protein level.
25. The method of any one of the paragraphs 15-24, wherein the level of SETDB1 is detected using an antibody-based binding agent which specifically binds to SETDB1 protein.
26. The method of any one of the paragraphs 15-25, further comprising measuring the expression level of at least one additional cancer marker.
27. The method of any one of the paragraphs 15-26, wherein the at least one additional cancer marker is p53 or BRAF.
28. The method of any one of the paragraphs 15-27, wherein the BRAF comprises an activating mutation.
29. The method of any one of the paragraphs 15-28, wherein the activating mutation comprises $BRAF^{V600E}$.
30. A computer readable storage medium having computer readable instructions recorded thereon to define software modules including a determination system and a comparison module for implementing a method on a computer for diagnosing a subject with cancer, the method comprising:
  (a) storing data derived from a biological sample obtained from a subject and which represents expression data for SETDB1 from a biological sample,
  (b) comparing with the comparison module the data stored on the storage device with reference and/or control data, and to provide a retrieved content, and
  (c) displaying the retrieved content for the user, wherein the retrieved content is indicative that the subject has cancer if the level of SETDB1 in the biological sample is higher than the reference data, and wherein the retrieved content is indicative that the subject is free from cancer if the level of SETDB1 in the biological sample is lower than the reference data.
31. A computer system for obtaining expression data for SETDB1 in a biological specimen comprising:
  (a) a determination system configured to receive expression information for SETDB1 from a biological sample obtained from a subject;
  (b) a storage device configured to store data output from the determination system;
  (c) a comparison module adapted to compare the data stored on the storage device with reference and/or control data, and to provide a retrieved content, and
  (d) a display module for displaying the retrieved content for the user, wherein the retrieved content is indicative that the subject has cancer if the level of SETDB1 in the biological sample is higher than the reference data, and wherein the retrieved content is indicative that the subject is free from cancer if the level of SETDB1 in the biological sample is lower than the reference data.
32. A kit for measuring SETDB1 expression in a biological sample, the kit comprising:
  (a) an agent that selectively binds SETDB1,
  (b) packaging materials and instructions for measuring SETDB1 expression in a sample.
33. The kit of paragraph 32, wherein the agent comprises a detectable moiety.
34. The kit of paragraph 32 or 33, further comprising an SETDB1 positive control.
35. The kit of any one of the paragraphs 32-34, wherein the kit is an ELISA kit.
36. The kit of any one of the paragraphs 32-35, wherein the agent comprises an antibody or a nucleic acid probe.
37. A method for delaying onset of melanoma or invasiveness of melanoma in a subject, the method comprising: administering an inhibitor of SETDB1 to a subject suspected of having, or diagnosed as having melanoma.
38. The method of paragraph 37, wherein the SETDB1 inhibitor is administered orally.
39. The method of paragraph 37 or 38, wherein the SETDB1 inhibitor is administered topically.
40. The method of any one of the paragraphs 37-39, wherein the subject is a mammal.
41. The method of any one of the paragraphs 37-40, wherein the subject is a human.
42. The method of any one of the paragraphs 37-41, further comprising a step of selecting a subject having cancer.
43. The method of any one of the paragraphs 37-42, wherein the selecting step comprises comparing the level of SETDB1 in a sample obtained from a subject to a reference, wherein an increase in SETDB1 level in the sample compared to the reference is indicative of cancer in the subject.
44. The method of any one of the paragraphs 37-43, further comprising measuring the expression level of at least one additional cancer marker.
45. The method of any one of the paragraphs 37-44, wherein the at least one additional cancer marker is p53 or BRAF.
46. The method of any one of the paragraphs 37-45, wherein the BRAF comprises an activating mutation.
47. The method of any one of the paragraphs 37-46, wherein the activating mutation comprises $BRAF^{V600E}$.

EXAMPLES

Summary

Melanoma is an aggressive malignancy in which treatment options are limited for patients with metastatic disease. In an effort to identify novel melanoma oncogenes a screen using a transgenic zebrafish model system was designed. A transgenic system was created in which a specialized vector, termed MiniCopR, delivers a candidate oncogene and also rescues melanocytes in the nacre mutant strain which is deficient in melanocytes. In this system zebrafish embryos which were productively injected are followed for tumor development. The MiniCopr system was utilized to test 15 candidate genes that are amplified and overexpressed in human melanomas on chromosome 1q21.3, a locus of common melanoma copy gain, and an addition set of 30 genes from other amplified regions. Each candidate oncogene was tested for cooperativity with $BRAF^{V600E}$; $p53^{-/-}$ for the rate of tumor formation. The screen identified SETDB1, an H3K9 histone methyltransferase, as a gene in the 1q21.3 interval that cooperates with $BRAF^{V600E}$; $p53^{-/-}$ to increase the rate of tumor formation.

Example 1

The most common mutation in melanoma, BRAFV600E, activates the BRAF serine/threonine kinase, and causes excessive MAPK pathway activity (Davies, H. et al., *Nature* 417 (6892), 949-954 (2002); Wan, P. T. et al., *Cell* 116 (6), 855-867 (2004)) BRAFV600E mutations are also present in benign melanocytic nevi (Pollock, P. M. et al., *Nat Genet* 33 (1), 19-20 (2003)), highlighting the importance of additional genetic alterations in the genesis of malignant tumors. Additional alterations may include recurrent copy number variations that result in the amplification of oncogenes (Curtin, J. A. et al., *N Engl J Med* 353 (20), 2135-2147 (2005); Garraway, L. A. et al., *Nature* 436 (7047), 117-122 (2005)). For certain amplifications, the large number of genes in the interval has precluded an understanding of cooperating oncogenic events. A zebrafish melanoma model was used to test genes in a recurrently amplified region on chromosome 1 for the ability to cooperate with BRAFV600E and accelerate melanoma. SETDB1, an enzyme that methylates histone H3 on lysine 9 (H3K9), was found to significantly accelerate melanoma formation in the zebrafish. Chromatin immunoprecipitation coupled with massively parallel DNA sequencing (ChIP-Seq) and gene expression analyses revealed target genes, including Hox genes, that are transcriptionally dysregulated in response to elevated SETDB1. These studies establish SETDB1 as an oncogene in melanoma and underscore the role of chromatin factors in regulating tumorigenesis.

Figure 1:
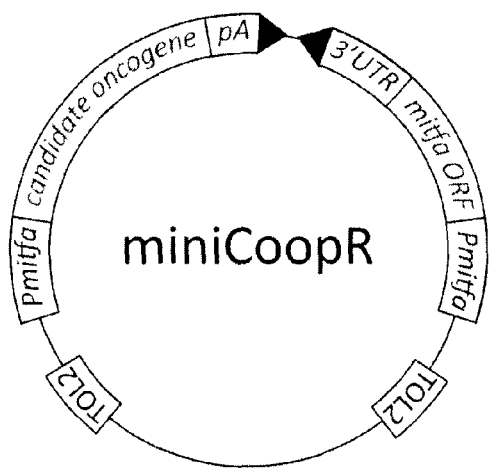
FIGS. 1A-1C SETDB1 accelerates melanoma formation in zebrafish 1A Schematic diagram of the miniCoopR vector used for testing candidate melanoma oncogenes. Pmitfa, a 2.1 kb fragment of the zebrafish mitfa gene promoter; TOL2, To12 transposon arms that mediate transposase-directed integration; pA, polyadenylation signal. 1B The Tg(mitfa:BRAFV600E); p53(lf); mitfa(lf) strain (left) injected with miniCoopR-cloned candidate oncogenes. Animals injected with miniCoopR-SETDB1 (right) have rescued melanocytes and rapidly develop melanomas (arrowhead). 1C Melanoma free survival curve of miniCoopR-SETDB1 (n=70) and mini-CoopR-EGFP (n=125) injected zebrafish.
Figure 1:
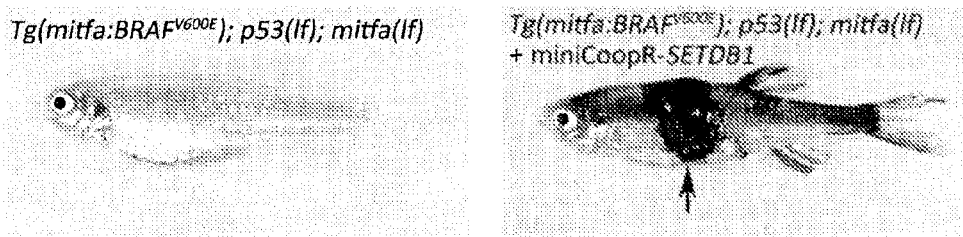
Figure 1:
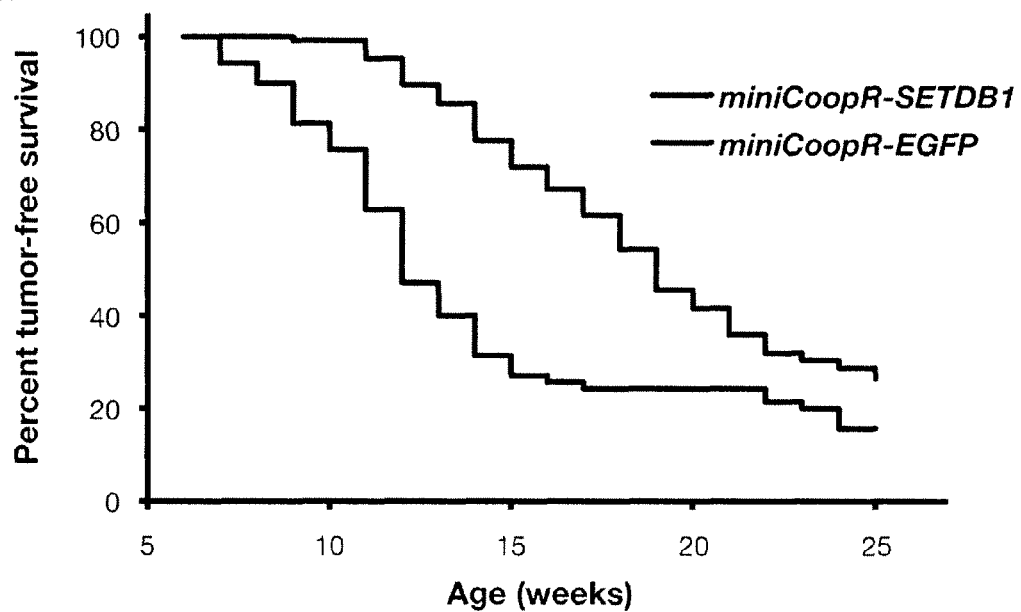
Figure 4:
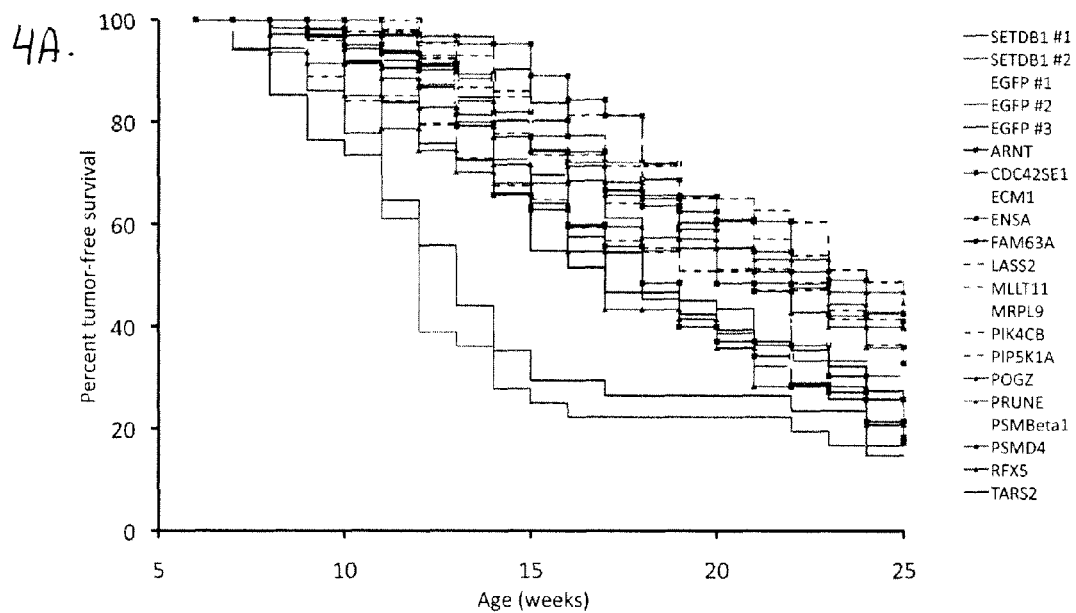
FIGS. 4A and 4B Melanoma free survival curves and median tumor incidence values for genes tested from the amplified chromosome 1q21 interval p values were derived from log rank χ2 values.

In order to identify cooperating oncogenes in melanoma, an assay was developed in transgenic zebrafish in which BRAFV600E is overexpressed on a p53 mutant background. Melanomas and melanocytes that develop in Tg(mitfa:BRAFV600E); p53(lf) zebrafish (Patton, E. E. et al., *Curr Biol* 15 (3), 249-254 (2005)) are suppressed by a mitfa(lf) mutation. A transposon-based vector, miniCoopR, was engineered that rescues melanocytes of a Tg(mitfa:BRAFV600E); p53(lf); mitfa(lf) strain and drives expression of a candidate gene in these cells (FIG. 1a). Genes from a human chromosome 1 interval (1q21; chr1:147.2-149.2 Mb) that are recurrently amplified and overexpressed at the mRNA level in melanoma (Lin, W. M. et al., *Cancer Res* 68 (3), 664-673 (2008)), were cloned into the miniCoopR vector and injected into one cell-stage Tg(mitfa:BRAFV600E); p53(lf); mitfa(lf) embryos. Tumor incidence curves of the resulting adults revealed that one gene in this interval, SETDB1, significantly accelerated melanoma onset (FIG. 1b,c and FIG. 4). Specifically, miniCoopR-EGFP injected animals had a median tumor onset of 19 weeks, whereas those injected with miniCoopR-SETDB1 had a median onset of 12 weeks (log rank χ2=24.1; p=9.4×10-7). No other gene accelerated melanomas, indicating SETDB1 is a critical gene amplified in the chromosome 1q21 interval.

Figure 5:
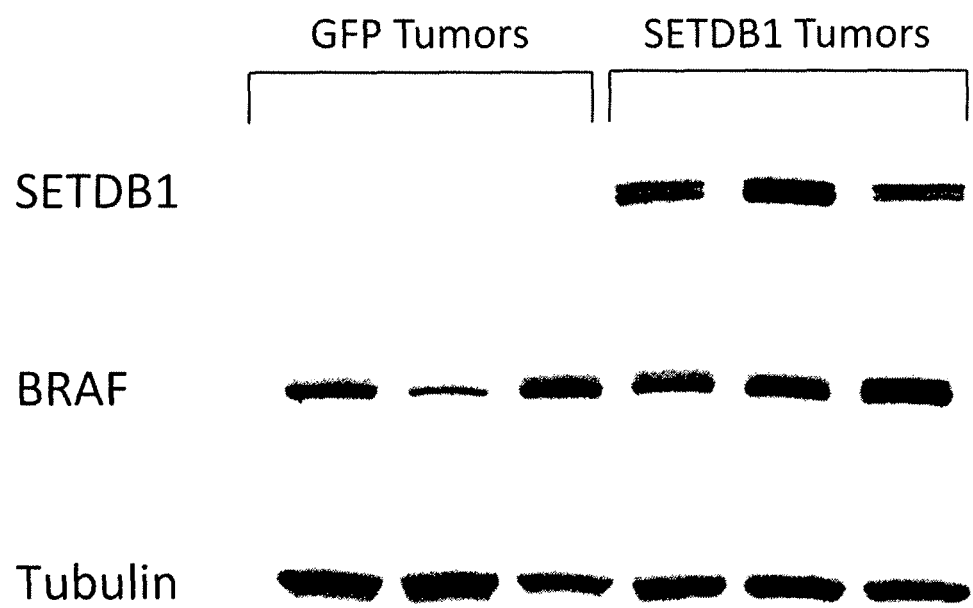
FIG. 5 BRAFV600E expression is not appreciably affected by SETDB1 expression

Melanomas overexpressing SETDB1 were more aggressive than control tumors when analyzed at an equivalent stage. Zebrafish with newly formed tumors on a strictly defined dorsal anterior location were isolated and the tumors permitted to develop for two weeks. The melanomas expressing SETDB1 were significantly more locally invasive than EGFP control tumors (data not shown); 94% (SETDB1) vs. 53% (EGFP) of melanomas invaded into the muscle (Fisher's Exact, p=1.6×10-3) and 89% (SETDB1) vs. 35% (EGFP) invaded into the spinal column (Fisher's Exact, p=7.2×10-3). MiniCoopR-SETDB1 melanomas had higher nuclear pleomorphism and a lower nuclear-to-cytoplasmic ratio compared with control tumors (data not shown). MiniCoopR-SETDB1 tumors showed similar levels of BRAF protein as compared to control tumors, indicating that SETDB1 did not accelerate melanoma formation by altering expression of the BRAFV600E oncogene used in the assays (FIG. 5).

Melanocytes overexpressing SETDB1 grew in confluent patches in zebrafish, unlike melanocytes in control zebrafish, which grew in a wild-type stripe pattern. To analyze the genetic interactions that are responsible for these pigmentation differences, miniCoopR-SETDB1 was injected into Tg(mitfa:BRAFV600E); mitfa(lf) and p53(lf); mitfa(lf) strains. The SETDB1-expressing melanocytes in the Tg(mitfa:BRAFV600E); mitfa(lf) strain formed confluent patches, but the SETDB1-expressing melanocytes in the p53 (lf); mitfa(lf) strain grew in a striped pattern (data not shown). Although SETDB1 and BRAFV600E cooperated to override normal pigment patterning, no tumors arose in miniCoopR-SETDB1 injected Tg(mitfa:BRAFV600E); mitfa(lf) zebrafish. Therefore, although SETDB1 and BRAFV600E can cooperate to form excess melanocytes, they require p53 loss of function to form tumors.

Oncogenic BRAFV600E induces senescence in human nevi and in cultured mammalian melanocytes (Michaloglou, C. et al., BRAFE600-associated senescence-like cell cycle arrest of human naevi. Nature 436 (7051), 720-724 (2005)), and it was hypothesized that the pigmentation differences results from a failure of senescence and excess melanocyte proliferation caused by SETDB1. To test this hypothesis senescence-associated β-Galactosidase (SA-βGal) staining (Dimri, G. P. et al., *Proc Natl Acad Sci USA* 92 (20), 9363-9367 (1995); Santoriello, C. et al., *Dis Model Mech* 2 (1-2), 56-67 (2009)) was performed on rescued melanocytes (data not shown). 76% of miniCoopR-EGFP rescued melanocytes generated in a Tg(mitfa:BRAFV600E); p53(lf); mitfa(lf) background were SA-βGal positive (n=224). However, only 14% of miniCoopR-SETDB1 rescued melanocytes were senescent (n=362). Without wishing to be bound by theory these results indicate that SETDB1 overexpression contributes to melanoma formation by abrogating oncogene-induced senescence.

Figure 2:
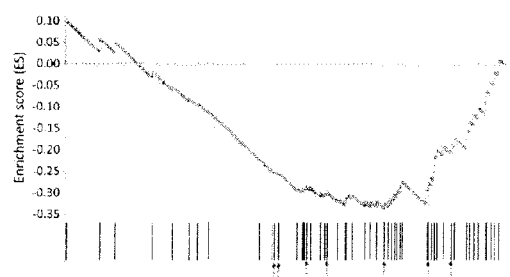
FIGS. 2A-2D Increased levels of SETDB1 alter expression of Hox and other target genes Heat map of genes downregulated in zebrafish melanomas that overexpress SETDB1 were compared with control (EGFP) melanomas (data not shown). 2A GSEA of SETDB1-downregulated gene set as applied to a panel of human melanomas stratified based on SETDB1 expression level. Homologs of zebrafish SETDB1-downregulated genes are similarly downregulated in human melanomas as levels of SETDB1 increase. 2B SETDB1 and H3K9me3 profiles at the HoxA locus in human melanoma cells. SETDB1 and H3K9me3 are present at HoxA in a melanoma with high SETDB1 expression (WM262) but diminished in a melanoma with low SETDB1 (WM451Lu). Protein binding and H3K9 modification density was measured in promoter-proximal regions (±5 kb of the transcriptional start site) of genes bound by SETDB1 (data not shown). Binding regions of SETDB1 are concordant with KAP1 and MCAF1, and all three overlap sites of H3K9me1 and H3K9me3 modifications. Gene expression and the patterns of SETDB1 binding and H3K9me3 mark in SETDB1 high (WM262) and low (WM451Lu) cells were compared (data not shown). The SETDB1 bound genes were rank ordered based on expression as measured from microarray experiments, with each gene normalized to the median level of expression (data not shown). Genes occupied by SETDB1 and histone H3K9me3 were determined (data not shown). 2C Venn diagram of genes bound by SETDB1 in SETDB1 high (WM262) and low (WM451Lu) cells identifies a set of genes bound in both melanomas. 2D Genes bound by SETDB1 in both high (WM262) and low (WM451Lu) cells used in GSEA and applied to a panel of human melanomas stratified based on SETDB1 expression level. SETDB1-bound genes generally increase in expression as levels of SETDB1 increase.
Figure 2:
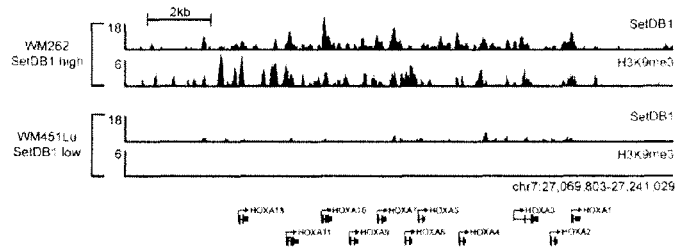
Figure 2:
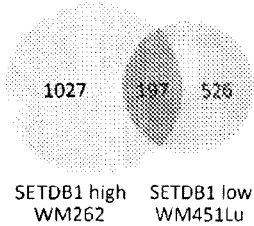
Figure 2:
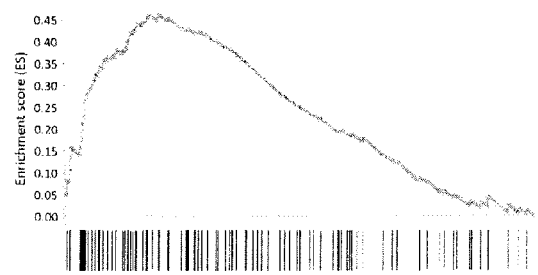

To understand the gene expression changes that occur when SETDB1 is overexpressed, microarray analyses of zebrafish melanomas were performed. As compared to control zebrafish melanomas, SETDB1 overexpressing melanomas were characterized by reduced expression of multiple transcription factors including members of the HOXA and HOXB locus, FOXD3, NSD1, and zinc finger transcription factors (data not shown). A gene signature comprising 69 human orthologs of genes downregulated in SETDB1 overexpressing melanomas was defined, and the relationship of this signature to SETDB1 expression in human melanoma was tested. Using gene set enrichment analysis (GSEA) (Subramanian, A. et al., *Proc Natl Acad Sci USA* 102 (43), 15545-15550 (2005); Mootha, V. K. et al., *Nat Genet* 34 (3), 267-273 (2003)) it was found that the gene signature was inversely correlated with SETDB1 expression across a panel of 93 melanoma short-term cultures and cell lines (FIG. 2a). SETDB1 overexpression leads to a broad pattern of transcriptional changes, including conserved downregulation of a group of genes enriched for transcriptional regulators.

Figure 8:
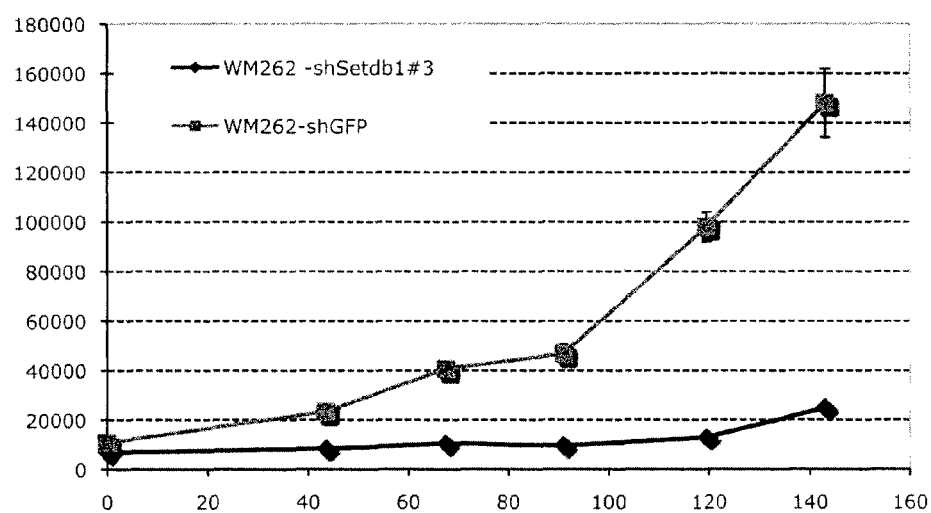
Figure 8:
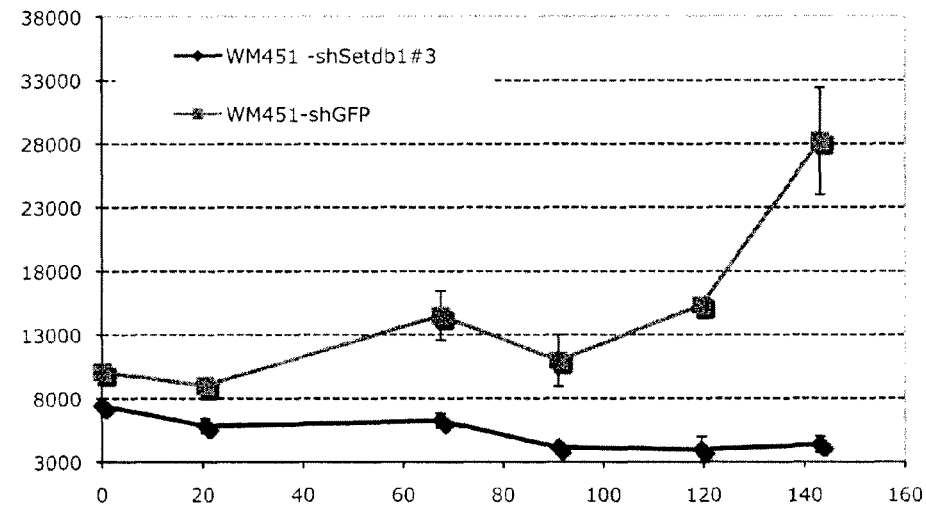

To define genome-wide targets of SETDB1 in melanoma, chromatin immunoprecipitation was performed followed by massively parallel sequencing (ChIP-Seq). SETDB1 targets were identified from WM262, a melanoma short-term culture with high SETDB1 expression, and WM451Lu, a melanoma short-term culture with low levels of SETDB1 (FIG. 6). These short-term cultures harbor the BRAFV600E mutation (FIG. 7) and depend on SETDB1 for proliferation (FIG. 8). In murine embryonic stem cells (mESCs), SETDB1 binds to the promoters of developmental regulators, including HOX genes (Bilodeau, S., et al. *Genes Dev* 23 (21), 2484-2489 (2009)). The authors observed differential binding of SETDB1 to genes in the HOXA cluster in melanoma cell lines with high vs. low SETDB1 expression; SETDB1 is bound to HOXA genes in WM262 cells, whereas there is minimal binding in WM451Lu cells (FIG. 2b). HOX gene expression is inversely correlated with SETDB1 levels in melanoma short-term cultures (FIG. 2a), indicating that enhanced target gene binding and repression may play a role in SETDB1-mediated melanoma acceleration.

SETDB1 is bound at genes that are marked by H3K9me3 and these genes are expressed at relatively low levels in both short-term cultures (data not shown). Analysis of the CHIP-Seq data in WM262 cells surprisingly revealed SETDB1 binding at many genes that are transcriptionally active and not marked by H3K9me3 (data not shown). To explore this further, the authors defined a set of genes that are bound in both SETDB1 high and low cells (FIG. 2c and Table 1) and determined how SETDB1 levels affect expression of these genes. This "bound-bound" gene set is positively correlated by GSEA with SETDB1 expression status across a panel of 93 melanoma short-term cultures (FIG. 2d). These data indicate that an increase in SETDB1 is associated with increased expression of SETDB1 bound genes.

TABLE 1

ACBD6
ACN9
ACP6
AEBP2
AGBL5
ALG8
ANKRD54
APEH
ARPM1
AVEN
B3GNT7
C10orf137
C10orf18
C11orf51
C11orf59
C12orf26
C12orf57
C15orf37
C16orf5
C1orf103
C1orf119
C1orf27
C3orf43
C3orf63
C6orf134
C7orf47
C7orf55
CCDC45
CCDC59
CCDC94
CELSR3
CENPA
CLTC
CNO
COPS6
COQ10B
CREB3L4
CRTC1
CSNK2A1
CSRP2BP
DDX5
DERL3
DHX40
DZIP3
EIF3EIP
EIF4A2
EIF5A2
ENPP3
ETHE1
EXTL2
FEM1C
FLOT1
GALNT4
GINS3

TABLE 1-continued

GSR
GSTCD
HIST1H1C
HLTF
HM13
HYAL1
HYAL2
IFT88
INTS12
JMJD1A
JMJD5
KHSRP
KIAA1524
KIAA1826
KRBA1
LACTB2
LBP
LIM2
LRRC40
LUC7L2
MAML2
MED23
MEFV
MEPCE
MGC16385
MORC2
MRFAP1L1
MRPS18B
MXI1
MYNN
N4BP2L2
N6AMT1
NANP
NASP
NDUFA4
NDUFS7
NPM1
NR3C1
NRBP2
NRSN2
NUP54
PAK1IP1
PBX3
PHF20
PI4K2B
PIK3CB
PIM1
PMF1
POLG2
PPP1R10
PRH1
PRR4
PTMA
PTPN6
PTPRH
RAD9B
RBM14
REEP3
RHEB
RPA2
RPL3
RPL31
RPP40
RPS18
RPS20
RQCD1
RTEL1
SAP130
SAP30
SDF2L1
SEPHS2
SEPT9
SETD4
SF3B14
SFRS1
SFRS11
SFRS6
SHFM1
SHQ1
SLC25A41

TABLE 1-continued

SLC30A7
SLC39A1
SLC46A2
SLCO4A1
SMG7
SPHK1
SPRY4
SR140
SSBP1
ST20
ST7
STX5
SUMO2

TABLE 1-continued

ZNF174
ZNF2
ZNF221
ZNF3
ZNF434
ZNF473
ZNF514
ZNF555
ZNF561
ZNF575
ZNF614
ZNF623
ZNF75A
ZRANB2

TABLE 2

| | Polyclonal Antibody Data | | Monoclonal Antibody Data | |
|---|---|---|---|---|
| Malignant Melanomas (n = 91) | | | Malignant Melanomas (n = 91) | |
| # Low (Score 0-4) | | 15 (16.5%) | # Low (Score 0-4) | 8 (8.6%) |
| # Medium (Score 5-8) | | 12 (13.2%) | # Medium (Score 5-8) | 13 (14.3%) |
| # High (Score 9-12) | | 64 (70.3%) | # High (Score 9-12) | 70 (78.9%) |
| Nevi (n = 20) | | | Nevi (n = 20) | |
| # Low (Score 0-4) | | 4 (20%) | # Low (Score 0-4) | 6 (25%) |
| # Medium (Score 5-8) | | 13 (65%) | # Medium (Score 5-8) | 11 (55%) |
| # High (Score 9-12) | | 3 (15%) | # High (Score 9-12) | 4 (25%) |
| Melanocytes of non-navic skin (n = 20) | | | Melanocytes of non-navic skin (n = 19) | |
| # Low (Score 0-4) | | 13 (65%) | # Low (Score 0-4) | 12 (63.2%) |
| # Medium (Score 5-8) | | 6 (30%) | # Medium (Score 5-8) | 6 (31.6%) |
| # High (Score 9-12) | | 1 (5%) | # High (Score 9-12) | 1 (6.3%) |
| Kappa Values: | | | | |
| For entire data set (both antibodies): | | 0.73 | | |
| Weighted kappa: | | 0.725 | | |

TABLE 1-continued

TAF7
TBX6
TESK1
TIGD7
TMED1
TMEM101
TMEM70
TMEM89
TOB2
TP53I3
TPR
TRIB1
TRIM44
TTC14
TTLL1
UBE2F
UBE2S
UQCRC1
USP15
USP37
VPS29
VPS52
VRK3
WDR51B
WDR74
WDR89
WNK3
WWP1
XKR6
XKR9
YPEL3
ZC3H11A
ZCCHC7
ZCWPW1
ZDHHC5
ZNF134

To characterize the molecular complexes in which SETDB1 functions, CHIP-Seq was performed in WM262 cells with MCAF1/ATF71P, and KAP1, both well-characterized SETDB1 partner proteins (data not shown). MCAF1 binding is necessary for efficient conversion of H3K9me2 to H3K9me3 by SETDB1 (Wang, H. et al., *Mol Cell* 12 (2), 475-487 (2003)). KAP1 has been identified as a co-repressor that complexes with SETDB1 and binds to C2H2 zinc finger promoters (Schultz, D. C., *Genes Dev* 16 (8), 919-932 (2002); O'Geen, H. et al., *PLoS Genet* 3 (6), e89 (2007)). Analysis of the coordinate binding patterns of SETDB1, MCAF1, KAP1, and H3K9 methylation reveal overlap at the transcriptional start site of many SETDB1 bound genes (data not shown) consistent with the formation of a chromatin complex involved in gene repression. However, many SETDB1 targets are bound by neither MCAF1 nor KAP1, and are less commonly methylated at H3K9 compared with the SETDB1/MCAF1/KAP1 bound genes (FIG. 9). Using GSEA a positive relationship was identified between genes solely bound by SETDB1 and SETDB1 expression levels in melanoma short term cultures (FIG. 10). These data identify two distinct patterns of SETDB1 binding in melanoma. Evidence was observed for a SETDB1/MCAF1/KAP1 complex associated with H3K9 methylation, consistent with a role in gene repression. Furthermore evidence of SETDB1 binding in the absence of MCAF1 and KAP1 was observed, and this set of genes appears to be transcriptionally upregulated in melanoma cell lines with increasing levels of SETDB1.

Without wishing to be bound by theory, these results indicate that SETDB1 has a role in chromatin regulation that is distinct from H3K9 methyltransferase-mediated repression and may involve, either directly or indirectly, gene activation.

To test this concept two mutations were engineered (H1224K and C1226A) into SETDB1 that disrupt histone methyltransferase activity (Schultz, D. C., *Genes Dev* 16 (8), 919-932 (2002)). Tumor incidence curves from two methyltransferase-deficient SETDB1 mutants are similar to each other and to wild-type SETDB1 (FIG. 11). These data indicate that overexpression of methyltransferase-independent activity of SETDB1 may contribute to acceleration of melanoma. Endogenous zebrafish Setdb1 was present in these experiments, so without wishing to be bound by theory melanoma acceleration may have resulted from a combination of methyltransferase-dependent and independent activities.

Figure 3:
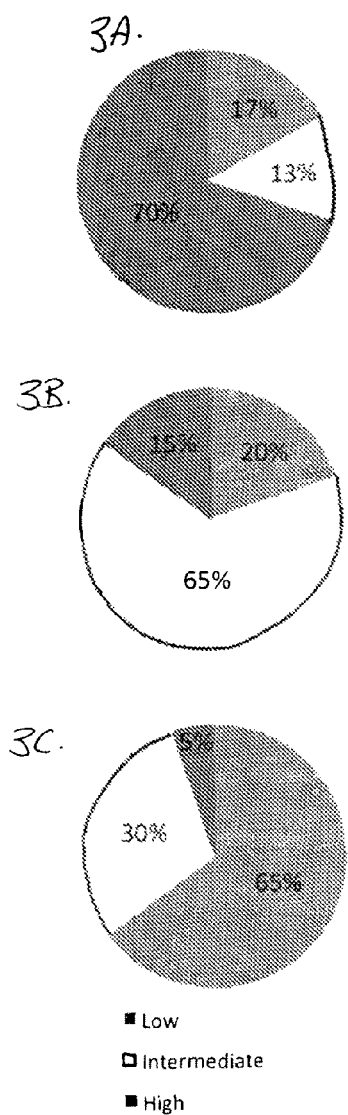
FIGS. 3A-3C High expression of SETDB1 protein is common in human melanomas but not nevi or normal melanocytes Immunohistochemical staining of SETDB1, hematoxylin and eosin (H+E) staining and SETDB1 expression was performed and scored on malignant melanoma, nevus and normal skin (data not shown). The pie diagrams indicate SETDB1 expression in malignant melanoma (3A), nevus (3B) and normal skin (3C).

To determine the extent of SETDB1 overexpression in human melanomas, and to examine potential clinical implications, immunohistochemistry (IHC) was performed on melanoma tissue microarrays. Two anti-SETDB1 antibodies were validated on human and zebrafish melanomas, showing that they specifically recognize SETDB1 protein and produce concordant staining patterns (data not shown). High levels of SETDB1 expression were seen in 5% of normal melanocytes, 15% of benign nevi, and 70% of malignant melanoma (FIG. 3). Without wishing to be bound by theory, it is speculated that nevi harboring SETDB1 overexpression have a higher likelihood of oncogenic progression as compared with nevi which show basal levels of expression. These data indicate that the majority of malignant melanomas demonstrate overexpression of SETDB1 protein.

This study illustrates the strength of using zebrafish to screen for oncogenes and characterize cancer phenotypes. Using zebrafish over 3000 transgenic animals were created and analyzed to functionally test genes for the ability to accelerate tumor formation. SETDB1 was identified as an important gene in the chromosome 1q21 interval capable of accelerating melanoma formation in cooperation with BRAFV600E. This study indicates that overexpression of SETDB1 leads to a broad pattern of gene expression changes, both activation and repression. These gene expression changes allow melanoma cells to accelerate or bypass early steps in tumorigenesis. SETDB1 has been shown to promote self-renewal in mESCs (Bilodeau, S., *Genes Dev* 23 (21), 2484-2489 (2009); Yuan, P. et al., *Genes Dev* 23 (21), 2507-2520 (2009)), leading the authors to hypothesize that SETDB1 overexpression enables nascent melanoma cells to acquire similar self-renewal characteristics. SETDB1 protein is overexpressed in a majority of melanomas and a small subset of nevi. The SETDB1 status of these melanocytic lesions indicates a distinct clinical behavior and response to therapy.

Methods miniCoopR Assay.

miniCoopR was constructed by inserting a zebrafish mitfa minigene (promoter+open reading frame+3'UTR) into the BglII site of pDestTol2pA2 (Kwan, K. M. et al., *Dev Dyn* 236 (11), 3088-3099 (2007)). Individual MiniCoopR clones were created by Gateway multisite recombination using human, full-length open reading frames (Invitrogen). Recombination junctions were sequence verified. 25 pg of each MiniCoopR-Candidate clone and 25 pg of to 12 transposase mRNA were microinjected into one-cell embryos generated from an incross of Tg(mitfa:BRAFV600E); p53(lf); mitfa(lf) zebrafish. Transgenic animals were selected based on the presence of rescued melanocytes at 48 hours post-fertilization. Rescued animals were scored weekly for the presence of visible tumor.

Tumor Invasion Assay.

Zebrafish with dorsal melanomas between the head and dorsal fin were isolated, and tumors were allowed to progress for two weeks, at which time animals were sacrificed. Tumors were formalin fixed, embedded, and sectioned transversely to assess invasion.

Senescence Assay.

SA-βGal staining was performed as described (Santoriello, C. et al., *Dis Model Mech* 2 (1-2), 56-67 (2009)), except that scales plucked from the dorsum of melanocyte-rescued zebrafish were stained instead of tissue sections. This assay was performed in an albino(b4) mutant background so melanin pigment would not obscure βGal staining. Experimental animals were injected with 20 pg miniCoopR-SETDB1+10 pg miniCoopR-EGFP and controls with 30 pg miniCoopR-EGFP. Rescued melanocytes were recognized as EGFP-positive cells.

Gene Expression.

Total RNA was extracted from four zebrafish miniCoopR-SETDB1 melanomas and four zebrafish miniCoopR-EGFP melanomas. 20 ug total RNA from each was amplified and hybridized to a Nimblegen 385K array (catalog 071105_Zv7_EXPR). Zebrafish genes downregulated by SETDB1 were selected by fold change (EGFP/SETDB1)>5 and filtered by a 'SETDB1 specificity score', which was defined as the fold change in zebrafish melanomas from Tg(mitfa:BRAFV600E); p53(lf)/MiniCoopR-SETDB1>3. Human orthologs were identified for GSEA analysis, which was performed using expression profiles of 93 melanoma cell lines and short term cultures as previously reported (Lin, W. M. et al., *Cancer Res* 68 (3), 664-673 (2008)).

Chromatin Immunoprecipitation.

Chromatin immunoprecipitation was performed from short term cultures of WM262 and WM451Lu as previously described (Bilodeau, S., *Genes Dev* 23 (21), 2484-2489 (2009)).

Immunohistochemistry.

Human melanoma tissue microarrays (TMAs) were analyzed by immunohistochemistry for SETDB1 using rabbit polyclonal Ab (Sigma HPA018142, 1:200) and a mouse monoclonal Ab 4A3 (Sigma, WH0009869M7, 1:400). SETDB1 immunostaining was also performed on formalin fixed, parrafin embedded zebrafish melanomas. Melanoma TMAs were obtained from U.S. Biomax (ME1003, ME482).

Results

SETDB1 Effects on Melanoma Cells and Melanocytes

Hematoxylin and eosin stained transverse sections of zebrafish melanomas were assessed at two weeks post onset. At this time point dorsal miniCoopR-EGFP melanomas display exophytic growth, whereas miniCoopR-SETDB1 melanomas have invaded from the skin into the underlying musculature (data not shown).

SETDB1 interacts with BRAFV600E to affect pigmentation pattern, but a p53(lf) mutation is required to form melanomas. MiniCoopR-EGFP or MiniCoopR-SETDB1 was injected into the indicated transgenic strain. The percent melanoma incidence at 25 weeks of age was 10% in Tg(mitfa:BRAF$^{V600E}$); p53(lf); mitfa(lf) fish treated with miniCoopR-EGFP, 53% in Tg(mitfa:BRAF$^{V600E}$); p53(lf); mitfa(lf) fish treated with miniCoopR-SETDB1. No melanoma was detected in Tg9mitfa:BRAFV600E); mitfa(lf) fish or p53(lf); mitfa(lf) fish treated with miniCoopR-SETDB1 (data not shown).

SETDB1 abrogates BRAFV600E-induced senescence. Brightfield photomicrographs were taken of SA-βGal staining performed on scale associated melanocytes (data not shown). Fluorescent photomicrographs performed on the same melanocytes showed that miniCoopR-rescued melanocytes express mitfa promoter driven EGFP and the MITFA protein (data not shown). Multiple nuclei were present in BRAFV600E-expressing melanocytes (data not shown).

miniCoopR-SETDB1 Melanomas Display Nuclear Pleomorphism and Low Nucleo-Cytoplasmic Ratio Melanomas expressing SETDB1 have greater nuclear pleomorphism and lower nuclear-to-cytoplasmic ratio than control EGFP-expressing melanomas.

SETDB1 Antibody Specificity

Immunohistochemistry was performed on zebrafish melanomas from miniCoopR-EGFP or miniCoopR-SETDB1 animal (data not shown). Two independent antibodies were identified which recognize human SETDB1 protein in miniCoopR-SETDB1 melanomas. Immunohistochemistry performed on human nevi demonstrate similar staining using two independent anti-SETDB1 antibodies, and H+E staining was performed (data not shown).

The invention claimed is:

1. A method for facilitating the diagnosis of lung cancer or melanoma in a subject, the method comprising:
    selecting a subject having at least one solid tumor or growth or a nevus;
    measuring the level of SETDB1 in a biological sample obtained from the subject who has at least one solid tumor or growth or a nevus,
        wherein the biological sample is derived from the at least one solid tumor or growth or nevus from the subject wherein the level of SETDB1 is detected at the mRNA level by a PCR procedure or at the protein level by an immunoassay and;
    identifying the likelihood of cancer in the subject by comparing the measured level of SETDB1 to a reference level,
        wherein the reference level is the level of SETDB1 in a subject or group of subjects who are clinically free of cancer and the level of SETDB1 in the cancer-free subject(s) is detected in the same manner as the measured subject, either at the mRNA level by a PCR procedure or at the protein level by an immunoassay; and
    determining whether the subject has cancer and therefore requiring cancer treatment or whether the subject has a benign growth based upon the comparison wherein an increase of at least 10% in the SETDB1 level in the biological sample compared to the reference level is indicative of cancer in the subject.

2. The method of claim 1, wherein the at least one solid tumor or growth or nevus is benign.

3. The method of claim 2, wherein the benign nevus is a benign melanocytic nevus.

4. The method of claim 1, wherein the subject is a mammal.

5. The method of claim 1, wherein the subject is a human.

6. The method of claim 1, wherein the level of SETDB1 is detected using an antibody-based binding agent which specifically binds to SETDB1 protein.

7. The method of claim 1, further comprising selecting the subject for treatment with at least one anti-cancer agent if there is an increase of at least 10% in the SETDB1 level in the biological sample compared to the reference.

8. The method of claim 1, further comprising measuring the expression level of at least one additional cancer marker in the biological sample obtained from the subject if there is an increase of at least 10% in the SETDB1 level in the biological sample compared to the reference.

9. The method of claim 8, wherein the at least one additional cancer marker is p53 or BRAF.

10. The method of claim 9, wherein the BRAF comprises an activating mutation.

11. The method of claim 10, wherein the activating mutation comprises $BRAF^{V600E}$.

12. A method for facilitating the diagnosis of lung cancer or melanoma in a subject, the method comprising:
    selecting a subject having at least one solid tumor or growth or a nevus;
    measuring the level of SETDB1 in a biological sample obtained from a subject who has at least one solid tumor or growth or a nevus,
        wherein the biological sample is derived from the at least one solid tumor or growth or nevus and wherein the level of SETDB1 is detected at the mRNA level by a PCR procedure or at the protein level by an immunoassay;
    identifying the likelihood of cancer in the subject by comparing the measured level of SETDB1 to a reference level,
        wherein the reference level is the level of SETDB1 in a subject or group of subjects who are clinically free of cancer and the level of SETDB1 in the cancer-free subject(s) is detected in the same manner as the measured subject, either at the mRNA level or the protein level; and
    administering at least one anti-cancer agent to the subject when there is an increase of at least 10% in the SETDB1 level in the biological sample compared to the reference level, indicating cancer in the subject.

13. The method of claim 12, wherein the level of SETDB1 is detected using an antibody-based binding agent which specifically binds to SETDB1 protein.

* * * * *